US012594188B2

(12) United States Patent
Moriguchi et al.

(10) Patent No.: US 12,594,188 B2
(45) Date of Patent: Apr. 7, 2026

(54) OPHTHALMIC APPARATUS, METHOD OF CONTROLLING OPHTHALMIC APPARATUS, AND RECORDING MEDIUM

(71) Applicant: Topcon Corporation, Tokyo (JP)

(72) Inventors: Yoshikiyo Moriguchi, Tokyo (JP); Akiko Ishikawa, Tokyo (JP)

(73) Assignee: TOPCON CORPORATION, Tokyo (JP)

( * ) Notice: Subject to any disclaimer, the term of this patent is extended or adjusted under 35 U.S.C. 154(b) by 613 days.

(21) Appl. No.: 18/076,385

(22) Filed: Dec. 6, 2022

(65) Prior Publication Data

US 2023/0133949 A1 May 4, 2023

Related U.S. Application Data

(63) Continuation of application No. PCT/JP2021/018164, filed on May 13, 2021.

(30) Foreign Application Priority Data

Jun. 15, 2020 (JP) ................................. 2020-102771

(51) Int. Cl.
*A61F 9/008* (2006.01)

(52) U.S. Cl.
CPC .... *A61F 9/008* (2013.01); *A61F 2009/00851* (2013.01); *A61F 2009/00885* (2013.01); *A61F 2009/00897* (2013.01)

(58) Field of Classification Search
CPC ........... A61F 9/008; A61F 2009/00851; A61F 2009/00885; A61F 2009/00897; A61B 3/1035; A61B 3/102

(Continued)

(56) References Cited

U.S. PATENT DOCUMENTS 4,591,247 A * 5/1986 Kamiya ................. A61B 3/103
351/211
2011/0028953 A1 2/2011 Raksi et al.
(Continued)

FOREIGN PATENT DOCUMENTS

CN 102421351 A 4/2012
CN 102439426 A 5/2012
(Continued)

OTHER PUBLICATIONS

Extended European Search Report issued Jun. 20, 2024, in corresponding European Patent Application No. 1 21825371.4, 6pp.
(Continued)

*Primary Examiner* — William R Alexander
*Assistant Examiner* — Alaina Marie Swanson
(74) *Attorney, Agent, or Firm* — XSENSUS LLP

(57) ABSTRACT

An ophthalmic apparatus includes an interference optical system, an optical scanner controller, and a correction controller. The interference optical system includes an astigmatism correction optical member and an optical scanner, and is configured to split light from a light source into reference light and measurement light, to irradiate the measurement light onto the subject's eye via the astigmatism correction optical member and the optical scanner, and to detect interference light between returning light of the measurement light from the subject's eye and the reference light. The optical scanner controller is configured to control the optical scanner so as to deflect the measurement light in a horizontal direction and a vertical direction on a plane perpendicular to an optical axis of the interference optical system. The correction controller is configured to control the astigmatism correction optical member so as to correct astigmatism based on a detection result of the interference light obtained by the interference optical system.

16 Claims, 12 Drawing Sheets

(58) Field of Classification Search
USPC .................................................. 351/159.07
See application file for complete search history.

(56) References Cited

U.S. PATENT DOCUMENTS

| | | | |
|---|---|---|---|
| 2012/0044455 A1 | 2/2012 | Hirose | |
| 2015/0116663 A1* | 4/2015 | Kushida | A61B 3/0041 |
| | | | 351/206 |
| 2017/0135575 A1 | 5/2017 | Kobayashi | |
| 2017/0332899 A1 | 11/2017 | Walsh et al. | |
| 2019/0130170 A1* | 5/2019 | Makihira | G06T 7/0016 |
| 2020/0029805 A1 | 1/2020 | Seesselberg et al. | |
| 2021/0104313 A1 | 4/2021 | Mizobe et al. | |
| 2021/0161376 A1 | 6/2021 | Ono | |
| 2021/0224957 A1 | 7/2021 | Iwase et al. | |
| 2021/0390696 A1 | 12/2021 | Iwase et al. | |
| 2021/0398259 A1 | 12/2021 | Yamazoe et al. | |
| 2024/0321435 A1 | 9/2024 | Mizobe et al. | |

FOREIGN PATENT DOCUMENTS

| | | | |
|---|---|---|---|
| JP | 2010-279681 A | | 12/2010 |
| JP | 2013-500134 A | | 1/2013 |
| JP | 2013-81763 A | | 5/2013 |
| JP | 2015-29834 A | | 2/2015 |
| JP | 2016-22312 A | | 2/2016 |
| JP | 2016022312 A | * | 2/2016 |
| JP | 2018-68578 A | | 5/2018 |
| JP | 2018-158153 A | | 10/2018 |
| JP | 2019213740 A | | 12/2019 |
| JP | 2020048911 A | | 4/2020 |
| JP | 2020-72966 A | | 5/2020 |
| WO | 2016/002740 A1 | | 1/2016 |
| WO | 2020075345 A1 | | 4/2020 |

OTHER PUBLICATIONS

Japanese Office Action issued Dec. 10, 2024, in corresponding Japanese Patent Application No. 2024-090379, 6pp.

International Search Report and Written Opinion mailed on Jul. 27, 2021, received for PCT Application PCT/JP2021/018164, filed on May 13, 2021, 8 pages including English Translation.

Office Action issued on Apr. 9, 2024, in corresponding Japanese patent Application No. 2020-102771, 6 pages.

Japanese Office Action issued Apr. 1, 2025, in Japanese Patent Application No. 2024-117437, 8pp.

Japanese Office Action issued Oct. 28, 2025, in corresponding Japanese Patent Application No. 2025-013459, 8pp.

Chinese Office Action issued Jan. 30, 2026, in corresponding Chinese Patent Application No. 202180042426.1, 16pp.

* cited by examiner

OPHTHALMIC APPARATUS, METHOD OF CONTROLLING OPHTHALMIC APPARATUS, AND RECORDING MEDIUM

CROSS-REFERENCE TO RELATED APPLICATIONS

The present application is a continuation application of International Patent Application No. PCT/JP2021/018164, filed May 13, 2021, which claims priority to Japanese Patent Application No. 2020-102771, filed Jun. 15, 2020, both of which are herein incorporated by reference in their entirety.

FIELD

The disclosure relates to an ophthalmic apparatus, a method of controlling the ophthalmic apparatus, and a recording medium.

BACKGROUND

In recent years, attention has been drawn to optical coherence tomography (OCT) which is used to form images representing the surface morphology or the internal morphology of an object to be measured using light beam emitted from a laser light source or the like. Since OCT does not have invasiveness to human body as X-ray CT (Computed Tomography) does, development of application of OCT in medical field and biology field is particularly expected. For example, in the ophthalmic field, apparatuses for forming images of the fundus, the cornea, or the like have been in practical use.

In such an apparatus, the imaging conditions (measurement conditions) are adjusted before OCT is performed in order to obtain images which are optimal for observing the morphology of the object to be measured (for example, Japanese Unexamined Patent Publication No. 2016-022312 and International Publication WO2016/002740). Adjustment of imaging conditions includes adjustment of a position of the imaging site, focus adjustment, and polarization adjustment. In particular, International Publication WO2016/002740 discloses a method of adjusting the imaging conditions by performing a raster scan in a shorter time than the time required for the raster scan performed at the imaging.

SUMMARY

One aspect of some embodiments is an ophthalmic apparatus, includes: an interference optical system including an astigmatism correction optical member and an optical scanner, and configured to split light from a light source into measurement light and reference light, to irradiate the measurement light onto a subject's eye via the astigmatism correction optical member and the optical scanner, and to detect interference light between returning light of the measurement light from the subject's eye and the reference light; an optical scanner controller configured to control the optical scanner so as to deflect the measurement light in a horizontal direction and a vertical direction on a plane perpendicular to an optical axis of the interference optical system; and a correction controller configured to control the astigmatism correction optical member so as to correct astigmatism based on a detection result of the interference light obtained by the interference optical system.

Another aspect of some embodiments is a method of controlling an ophthalmic apparatus including an interference optical system including an optical scanner and configured to split light from light source into measurement light and reference light, to irradiate a subject's eye with the measurement light deflected by the optical scanner, and to detect interference light between returning light of the measurement light from the subject's eye and the reference light. The method of controlling the ophthalmic apparatus includes a first control step of controlling the optical scanner so as to deflect the measurement light in a horizontal direction and a vertical direction on a plane perpendicular to an optical axis of the interference optical system; and a second control step of controlling the astigmatism correction optical member so as to correct astigmatism based on a detection result of the interference light obtained in the interference optical system by irradiating the measurement light deflected in the first control step onto the subject's eye.

Still another aspect of some embodiments is a non-transitory computer readable recording medium storing a program of causing a computer to execute each step of the method of controlling the ophthalmic apparatus described above.

DETAILED DESCRIPTION

Figure 1:
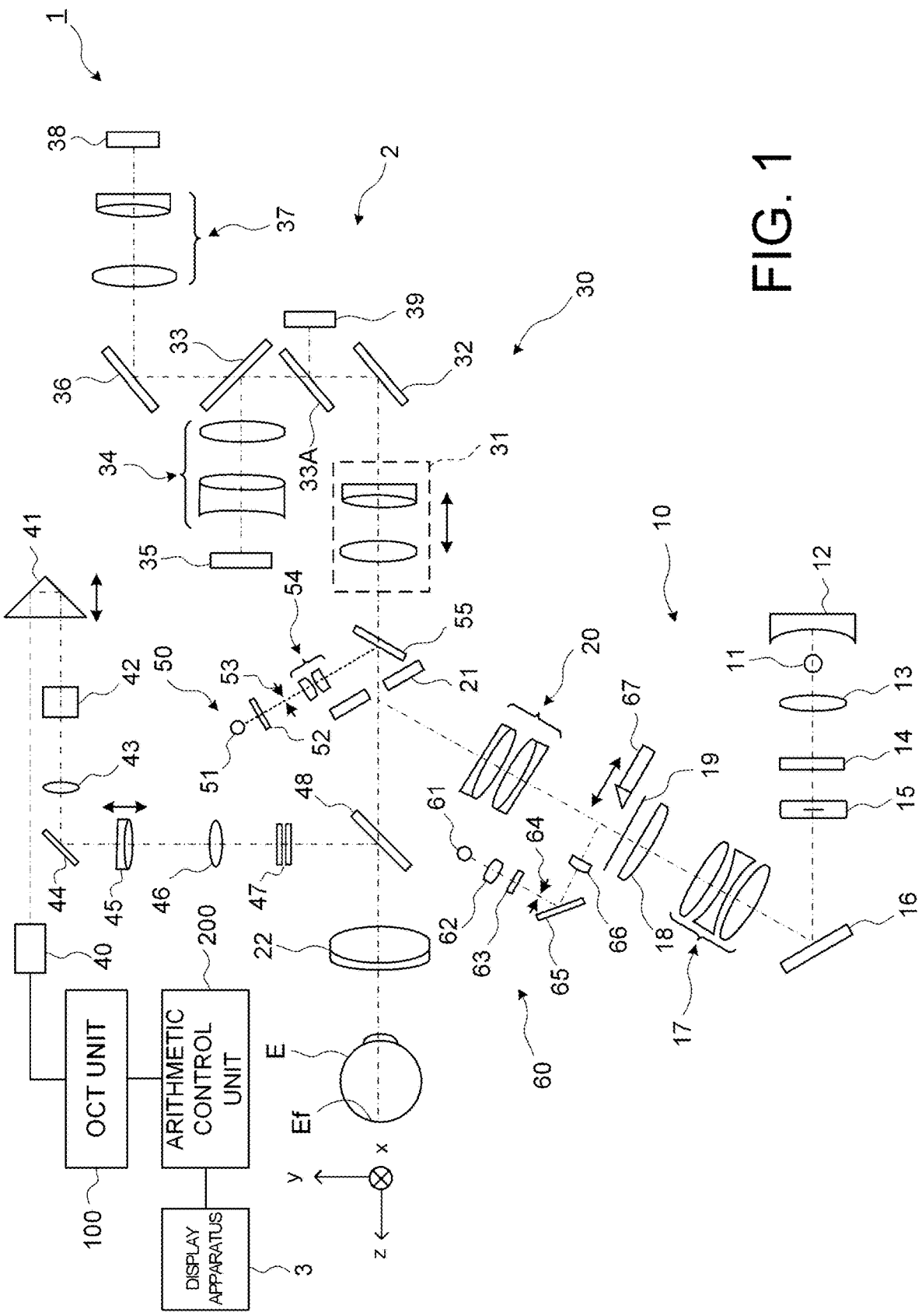
FIG. 1 is a schematic diagram illustrating an example of a configuration of an optical system of an ophthalmic apparatus according to embodiments.

In recent years, the speed of light sources has been increasing. Thereby, bottlenecks have begun to appear in the operating speed of the optical scanner for scanning the imaging site of OCT. As the speed of light sources increases, it becomes even more difficult to adjust the imaging conditions with high precision in raster scans with long scan times.

According to some embodiments according to the present invention, a new technique for adjusting imaging condition(s) with high precision even when the speed of light sources is increased can be provided.

In the following detailed description, for purposes of explanation, numerous specific details are set forth in order to provide a thorough understanding of the disclosed embodiments. It will be apparent, however, that one or more embodiments may be practiced without these specific details. In other instances, well-known structures and devices are schematically shown in order to simplify the drawing.

Referring now to the drawings, exemplary embodiments of an ophthalmic apparatus, a method of controlling the ophthalmic apparatus, and a recording medium according to the present invention are described below. Any of the contents of the documents cited in the present specification and arbitrary known techniques may be applied to the embodiments below.

An ophthalmic apparatus according to embodiments includes an interference optical system, scans a subject's eye with measurement light deflected using an optical scanner, and adjusts imaging (shooting) condition(s) based on a detection result of acquired interference light. The interference optical system is configured to split light from a light source into reference light and measurement light, to irradiate the measurement light onto the subject's eye via the optical scanner, and to detect interference light between returning light of the light from the subject's eye and the reference light. The optical scanner is configured to deflect the measurement light according to a predetermined scan pattern (deflection pattern). Examples of the adjustment of the imaging condition include an adjustment of a position of an imaging site, a focus adjustment, a polarization adjustment, and a correction of astigmatism.

In some embodiments, the interference optical system includes an astigmatism correction optical member (astigmatism correction member). The optical scanner deflects the measurement light in a horizontal direction and a vertical direction on a plane perpendicular to an optical axis of the interference optical system. The optical scanner according to some embodiments deflects the measurement light in a meridional direction and a sagittal direction. The meridional direction is a concentric direction around the optical axis of the interference optical system. The sagittal direction is a radial direction around the optical axis of the interference optical system. The ophthalmic apparatus corrects astigmatism based on a detection result of the interference light obtained by scanning the subject's eye with the measurement light deflected by the optical scanner.

Examples of the astigmatism correction optical member include a variable cross cylinder (hereinafter referred to as VCC) lens, a liquid crystal lens, a deformable mirror, an Alvarez lens, etc.

This allows to acquire information in the above horizontal direction and information in the above vertical direction with fewer scans than for the raster scan (two or more line scans). Therefore, the information in the horizontal direction and the information in the vertical direction can be acquired in a shorter time than the time required for raster scan, and the astigmatism can be corrected from the acquired information in the horizontal and the acquired information in the vertical direction. Here, the time required for the raster scan is equivalent to the sum of the time required for a plurality of line scans and the time required for flyback between each line scan, for example. In other words, according to the embodiments, the astigmatism can be corrected with high precision without being affected by eye movement or other factors, even when the speed of the light source is increased.

In particular, by employing circle scan as a scan mode for deflecting the measurement light in the horizontal direction and vertical direction on the plane perpendicular to the optical axis of the interference optical system, the scan speed can be kept approximately constant over the entire scan region. This makes it possible to acquire homogeneous scan results over the entire scan region and to correct the astigmatism with high precision based on the homogeneous scan results. In addition, the astigmatism can be corrected with high precision based on the artifact-free scan results, since it is less affected by the specular reflection from the apex of the objective lens.

In some embodiments, the interference optical system includes a focusing position changing member capable of changing a focal position of the measurement light. The ophthalmic apparatus is configured to scan the subject's eye with the measurement light deflected using the optical scanner, and controls the focusing position changing member based on the detection result of the acquired interference light. The deflection pattern of the measurement light may be any pattern. For example, the ophthalmic apparatus controls the focusing position changing member based on the detection result of the interference light obtained by scanning the subject's eye with the measurement light deflected in a line direction intersecting the optical axis of the interference optical system or with the measurement light deflected in the horizontal and vertical directions on the plane perpendicular to the optical axis of the interference optical system.

Examples of the focusing position changing member include a lens capable of moving along the optical axis, a liquid crystal lens, and an Alvarez lens, etc.

In some embodiments, the interference optical system includes an optical path length changing member for changing an optical path length difference between the measurement light and the reference light. The ophthalmic apparatus is configured to scan the subject's eye with the measurement light deflected using the optical scanner, and to control the optical path length changing member based on the detection result obtained by the acquired interference light. The deflection pattern of the measurement light may be any pattern. For example, the ophthalmic apparatus controls the optical path length changing member based on the detection result of the interference light obtained by scanning the subject's eye with the measurement light deflected in a line direction intersecting the optical axis of the interference optical system or with the measurement light deflected in the horizontal and vertical directions on the plane perpendicular to the optical axis of the interference optical system.

In some embodiments, the interference optical system includes a polarization state changing member for changing a polarization state of the measurement light or a polarization state of the reference light. The ophthalmic apparatus is configured to scan the subject's eye with the measurement light deflected using the optical scanner, and to control the polarization state changing member based on the detection result of the acquired interference light. The deflection pattern of the measurement light may be any pattern. For example, the ophthalmic apparatus controls the polarization state changing member based on the detection result of the interference light obtained by scanning the subject's eye with the measurement light deflected in a line direction intersecting the optical axis of the interference optical system or with the measurement light deflected in the horizontal and vertical directions on the plane perpendicular to the optical axis of the interference optical system.

A method of controlling the ophthalmic apparatus, the method according to the embodiments, is a method for controlling the ophthalmic apparatus according to the embodiments. A program according to the embodiments causes the processor to execute each step of the method of controlling the ophthalmic apparatus according to the embodiments. A recording medium according to the embodiments is a non-transitory recording medium on which the program according to the embodiments is recorded.

In the following embodiments, a circle scan will be described as an example of a scan mode for deflecting the measurement light in the horizontal and vertical directions on the plane perpendicular to the optical axis of the interference optical system. However, the embodiments also can be applied to cases where the measurement light is deflected with a scan pattern other than the circle scan.

The ophthalmic apparatus according to the embodiments can perform OCT on an arbitrary site of the subject's eye, such as the fundus, or the anterior segment, for example. In this specification, an image acquired using OCT may be collectively referred to as an "OCT image". Also, the measurement operation for forming OCT images may be referred to as OCT measurement.

Hereinafter, in the embodiments, a case of using the swept source type OCT method in the measurement or the imaging (shooting) using OCT will be described. However, the configuration according to the embodiments can also be applied to an ophthalmic apparatus using other type of OCT (for example, spectral domain type OCT or time domain OCT).

[Configuration]

Figure 2:
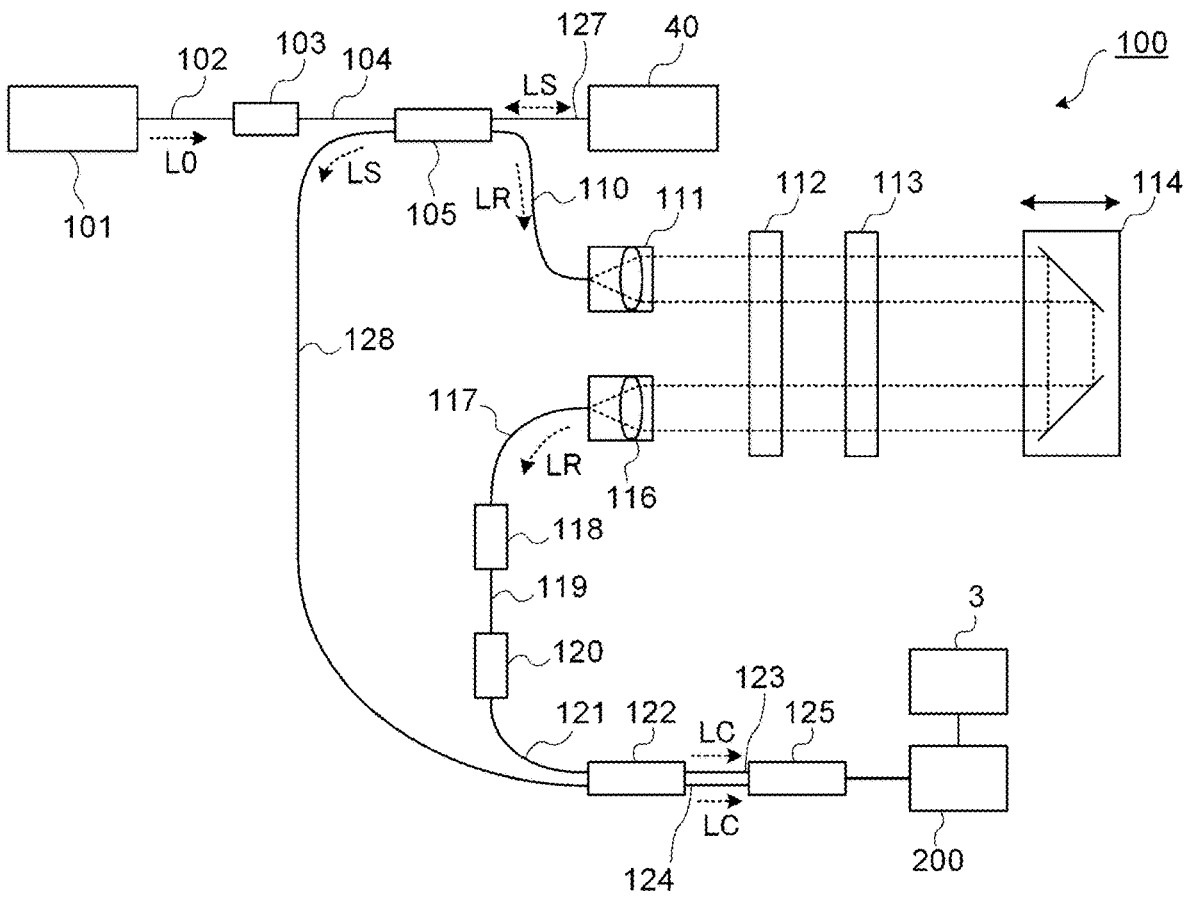
FIG. 2 is a schematic diagram illustrating an example of a configuration of an optical system of the ophthalmic apparatus according to the embodiments.
Figure 3:
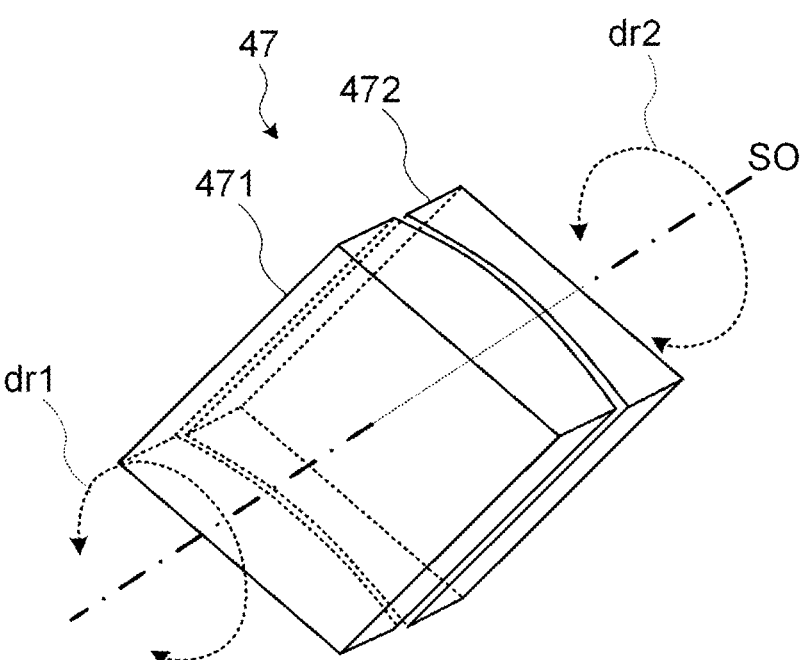
FIG. 3 is a schematic diagram illustrating an example of a configuration of an optical system of the ophthalmic apparatus according to the embodiments.

As shown in FIGS. 1 to 3, the ophthalmic apparatus 1 includes a fundus camera unit 2, an OCT unit 100, and an arithmetic control unit 200. The fundus camera unit 2 has substantially the same optical system as the conventional fundus camera. The OCT unit 100 is provided with an optical system for obtaining OCT images of the fundus (or the anterior segment). The arithmetic control unit 200 is provided a computer(s) that executes various kinds of arithmetic processing, control processing, and the like.

[Fundus Camera Unit 2]

The fundus camera unit 2 illustrated in FIG. 1 is provided with an optical system for acquiring two-dimensional images (fundus images) representing the surface morphology of a fundus Ef of a subject's eye E. Examples of the fundus images include observation images and photographic images. The observation image is, for example, a monochrome moving image formed at a predetermined frame rate using near-infrared light. The photographic image may be, for example, a color image captured by flashing visible light, or a monochrome still image using near-infrared light or visible light as illumination light. The fundus camera unit 2 may be configured to be capable of acquiring other types of images such as fluorescein angiograms, indocyanine green angiograms, and autofluorescent angiograms.

The fundus camera unit 2 is provided with a jaw holder and a forehead rest for supporting the face of the subject. Further, the fundus camera unit 2 is provided with an illumination optical system 10 and an imaging optical system 30. The illumination optical system 10 irradiates illumination light onto the fundus Ef. The imaging optical system 30 guides the illumination light reflected from the fundus Ef to an imaging device (i.e., the CCD image sensor 35 or 38). Each of the CCD image sensors 35 and 38 is sometimes simply referred to as a "CCD". Further, the imaging optical system 30 guides measurement light coming from the OCT unit 100 to the fundus Ef, and guides the measurement light returning from the fundus Ef to the OCT unit 100.

An observation light source 11 in the illumination optical system 10 includes, for example, a halogen lamp. Light (observation illumination light) emitted from the observation light source 11 is reflected by a reflective mirror 12 having a curved reflective surface, and becomes near-infrared light after passing through a visible cut filter 14 via a condenser lens 13. Further, the observation illumination light is once converged near an imaging light source 15, is reflected by a mirror 16, and passes through relay lenses 17 and 18, a diaphragm 19, and a relay lens 20. Then, the observation illumination light is reflected on the peripheral part (the surrounding area of the hole part) of the perforated mirror 21, is transmitted through a dichroic mirror 48, and refracted by the objective lens 22, thereby illuminating the fundus Ef. It should be noted that an LED (light emitting diode) may be used as the observation light source.

Fundus reflected light of the observation illumination light is refracted by the objective lens 22, is transmitted through the dichroic mirror 48, passes through the hole part formed in the center area of the perforated mirror 21, is transmitted through a dichroic mirror 55, travels through a focusing lens 31, and is reflected by a mirror 32. Further, this fundus reflected light is transmitted through a half mirror 33A, is reflected by a dichroic mirror 33, and forms an image on the light receiving surface of the CCD image sensor 35 by a condenser lens 34. The CCD image sensor 35 detects the fundus reflected light at a predetermined frame rate, for example. An image (observation image) based on the fundus reflected light detected by the CCD image sensor 35 is displayed on a display apparatus 3. It should be noted that when the imaging optical system 30 is focused on the anterior segment, an observation image of the anterior segment of the subject's eye E is displayed.

The imaging light source 15 includes, for example, a xenon lamp. Light (imaging illumination light) emitted from the imaging light source 15 is irradiated onto the fundus Ef via the same route as that of the observation illumination light. The fundus reflected light of the imaging illumination light is guided to the dichroic mirror 33 via the same route as that of the observation illumination light, is transmitted through the dichroic mirror 33, is reflected by a mirror 36, and forms an image on the light receiving surface of the CCD image sensor 38 by a condenser lens 37. The display apparatus 3 displays an image (photographic image) obtained based on the fundus reflected light detected by the CCD image sensor 38. It should be noted that the display apparatus 3 for displaying the observation image and the display apparatus 3 for displaying the photographic image may be the same or different. Besides, when similar imaging is performed by illuminating the subject's eye E with infrared light, an infrared photographic image is displayed. It is also possible to use an LED as the imaging light source.

A liquid crystal display (LCD) 39 displays a fixation target and a visual target used for visual acuity measurement. The fixation target is a visual target for fixating the subject's eye E, and is used when performing fundus imaging (photography) and OCT measurement.

Part of light emitted from the LCD 39 is reflected by the half mirror 33A, is reflected by the mirror 32, travels through the focusing lens 31 and the dichroic mirror 55, and passes through the hole part of the perforated mirror 21. The light having passed through the hole part of the perforated mirror 21 is transmitted through the dichroic mirror 48, and is refracted by the objective lens 22, thereby being projected onto the fundus Ef.

By changing the display position of the fixation target on the screen of the LCD 39, the fixation position of the subject's eye E can be changed. Examples of the fixation position of the subject's eye E include, as with conventional fundus cameras, a position for acquiring an image centered on the macula of the fundus Ef, a position for acquiring an image centered on the optic nerve head, a position for acquiring an image centered on the fundus center between the macula and the optic nerve head, and the like. Further, the display position of the fixation target may be changed to any desired position.

In addition, as with a conventional fundus camera, the fundus camera unit 2 is provided with the alignment optical system 50 and the focus optical system 60. The alignment optical system 50 generates an indicator (referred to as an alignment indicator) for the position adjustment (i.e., the alignment) of the optical system with respect to the subject's eye E. The focus optical system 60 generates a target (split target) for adjusting the focus with respect to the subject's eye E.

The light output from an LED 51 of the alignment optical system 50 (i.e., alignment light) travels through the diaphragms 52 and 53 and the relay lens 54, is reflected by the dichroic mirror 55, and passes through the hole part of the perforated mirror 21. The light having passed through the hole part of the perforated mirror 21 is transmitted through the dichroic mirror 48, and is projected onto the cornea of the subject's eye E by the objective lens 22.

Cornea reflected light of the alignment light travels through the objective lens 22, the dichroic mirror 48 and the hole part described above. Part of the cornea reflected light is transmitted through the dichroic mirror 55, and passes through the imaging focusing lens 31, is reflected by the mirror 32, and is transmitted through the half mirror 33A. The cornea reflected light transmitted through the half mirror 33A is reflected by the dichroic mirror 33, and forms an image on the light receiving surface of the CCD image sensor 35 by the condenser lens 34. The light receiving image (i.e., alignment indicator image) captured by the CCD image sensor 35 is displayed on the display apparatus 3 together with the observation image. The user conducts an alignment in the same manner as performed on a conventional fundus camera. Alternatively, alignment may be performed in such a way that the arithmetic control unit 200 analyzes the position of the alignment indicator and moves the optical system (automatic alignment).

To perform focus adjustment, a reflective surface of a reflection rod 67 is arranged in a slanted position on an optical path of the illumination optical system 10. The light output from a LED 61 in the focus optical system 60 (i.e., focus light) passes through a relay lens 62, is split into two light beams by a split indicator plate 63, passes through a two-hole diaphragm 64, and is reflected by a mirror 65. The focus light reflected by the mirror 65 is once converged on the reflective surface of the reflection rod 67 by the condenser lens 66, and is reflected by the reflective surface. Further, the focus light travels through the relay lens 20, is reflected by the perforated mirror 21, is transmitted through the dichroic mirror 48, and is refracted by the objective lens 22, thereby being projected onto the fundus Ef.

Fundus reflected light of the focus light passes through the same route as the cornea reflected light of the alignment light and is detected by the CCD image sensor 35. The display apparatus 3 displays the light receiving image (split indicator) captured by the CCD image sensor 35 together with the observation image. As in the conventional case, the arithmetic control unit 200 analyzes the position of the split indicator, and moves the focusing lens 31 and the focus optical system 60 for focusing (automatic focusing). Alternatively, the user may manually perform the focus adjustment while visually checking the split indicator image.

The dichroic mirror 48 branches the optical path for OCT measurement from the optical path for fundus imaging. The dichroic mirror 48 reflects light of wavelengths used for OCT measurement, and transmits light for fundus imaging. The optical path for OCT measurement is provided with, in order from the OCT unit 100 side, a collimator lens unit 40, an optical path length changing unit 41, an optical scanner 42, a collimate lens 43, a mirror 44, an OCT focusing lens 45, a field lens 46, a variable cross cylinder (hereinafter referred to as VCC) lens 47.

The optical path length changing unit 41 is configured to be capable of moving in a direction indicated by the arrow in FIG. 1, thereby changing the optical path length for OCT measurement. The change in the optical path length is used for the correction of the optical path length according to the axial length of the subject's eye E, and/or for the adjustment of the interference state, or the like. The optical path length changing unit 41 includes, for example, a corner cube and a mechanism for moving the corner cube.

The optical scanner 42 is disposed at a position conjugate optically to a pupil of the subject's eye E (pupil conjugate position) or near the position. The optical scanner 42 changes the traveling direction of light (measurement light) traveling along the optical path for OCT measurement. The optical scanner 42 can deflect the measurement light in a one-dimensionally or two-dimensional manner, under the control from the arithmetic control unit 200 described below.

The optical scanner 42 includes a first galvano mirror, a second galvano mirror, and a mechanism for driving them independently, for example. The first galvano mirror deflects the measurement light LS so as to scan the imaging site (fundus Ef or the anterior segment) in a horizontal direction (x direction) orthogonal to the optical axis of the OCT optical system 8. The x direction is a horizontal direction on a plane perpendicular to the optical axis of the interference optical system. The second galvano mirror deflects the measurement light LS deflected by the first galvano mirror so as to scan the imaging site in a vertical direction (y direction) orthogonal to the optical axis of the OCT optical system 8. The y direction is a vertical direction on the plane perpendicular to the optical axis of the interference optical system. Thereby, the imaging site can be scanned with the measurement light LS in any direction on the xy plane.

For example, by controlling the orientation of the first galvano mirror and the orientation of the second galvano mirror included in the optical scanner 42 at the same time, the irradiated position of the measurement light can be moved along an arbitrary trajectory on the xy plane. This allows to scan the imaging site according to a desired scan pattern.

The OCT focusing lens 45 is movable along the optical path of the measurement light LS (the optical axis of the interference optical system). The OCT focusing lens 45 moves along the optical path of the measurement light LS, under the control from the arithmetic control unit 200 described below.

In some embodiments, the liquid crystal lens or the Alvarez lens is provided instead of the OCT focusing lens 45. The liquid crystal lens or the Alvarez lens, as well as the OCT focusing lens 45, is controlled by the arithmetic control unit 200.

The VCC lens 47 is arranged on the optical path of the measurement light and changes at least one of the cylindrical power (astigmatism power) or the cylindrical axis angle (astigmatic axis angle). The VCC lens 47 has two cylindrical lenses (optical elements) positioned opposite each other, and is configured to change at least one of the cylindrical power or the cylindrical axis angle by changing at least one of the axial directions of the two cylindrical lenses. In the present embodiment, the two cylindrical lenses are configured to be capable of rotating independently so that the two axial directions are changed relative to each other. Further, the two cylindrical lenses are configured to be capable of rotating integrally while keeping the angle formed by the two axial directions.

The VCC lens 47 is disposed at a position conjugate optically to the pupil of the subject's eye (pupil conjugate position) or near the position. In the present embodiment, since the optical scanner 42 is disposed at the position conjugate optically to the pupil of the subject's eye, the VCC lens 47 is disposed near the position conjugate optically to the pupil of the subject's eye.

For the purpose of correcting the astigmatic power of the subject's eye E, even if the VCC lens 47 is disposed near the pupil conjugate position, it is reasonable to assume that a deviation of the VCC lens 47 relative to the pupil conjugate position has little effect on the cylindrical power or the cylindrical axis angle which are changed by the VCC lens 47.

When the VCC lens 47 is controlled based on the optometric data (objective measurement values or subjective inspection values) of the subject's eye E, the optometric data are mainly measured values on the fovea of the subject's eye E. However, it is reasonable to assume that the deviation of the arranged position of the VCC lens 47 relative to the pupil conjugate position has little effect on the cylindrical power or the cylindrical axis angle which are changed by the VCC lens 47. Therefore, even if the imaging site is different from the fovea, the VCC lens 47 may be positioned near the pupil conjugate position.

Such a VCC lens 47 is configured to include cylindrical lenses 471 and 472 with equal power and different signs from each other (focal lengths f0 and −f0), as shown in FIG. 3, for example. The cylindrical lens 471 (VCC1) has a convex surface (positive power), and is provided to be capable of rotating in a rotational direction dr1 around the optical path of measurement light LS (optical axis SO of the interference optical system). The cylindrical lens 472 (VCC2) has a concave surface (negative power), and is provided to be capable of rotating in a rotational direction dr2 around the optical axis SO. The cylindrical lenses 471 and 472 are driven by a driver such as a pulse motor, and are rotated independently around the optical axis SO. When the cylindrical lenses 471 and 472 are rotated in opposite directions to each other, the cylindrical power is changed, and when the cylindrical lenses 471 and 472 are rotated integrally in the same direction, the cylindrical axis angle is changed.

For example, the cylindrical lenses 471 and 472 are rotated in opposite directions to each other from a state in which the cylindrical axis angle of the cylindrical lenses 471 and 472 are tilted at a predetermined angle (e.g., 45 degrees) with respect to the optical axis SO. Thereby, arbitrary cylindrical power can be generated. Further, by rotating the cylindrical lenses 471 and 472 integrally in the same direction, arbitrary cylindrical axis angle can be generated.

[October Unit 100]

The configuration of the OCT unit 100 will be described with reference to FIG. 2. The OCT unit 100 is provided with an optical system for acquiring OCT images of the fundus Ef. The optical system has the same configuration as the conventional swept source type OCT apparatus. That is, the optical system includes an interference optical system configured to split light from a wavelength scanning type (wavelength sweeping type) light source into measurement light and reference light, to make the measurement light returned from the fundus Ef and the reference light having passed through a reference optical path interfere with each other to generate interference light, and to detect the interference light. The detection result (detection signal) of the interference light obtained by the interference optical system is a signal indicating the spectra of the interference light and is sent to the arithmetic control unit 200.

Like the general swept source type OCT apparatus, a light source unit 101 includes a wavelength scanning type (wavelength sweeping type) light source capable of scanning (sweeping) the wavelengths of emitted light. The light source unit 101 temporally changes the output wavelengths within the near-infrared wavelength bands that cannot be visually recognized with human eyes.

The light L0 emitted from the light source unit 101 is guided to the polarization controller 103 through the optical fiber 102, and the polarization state of the light L0 is adjusted. The polarization controller 103, for example, applies external stress to the looped optical fiber 102 to thereby adjust the polarization state of the light L0 guided through the optical fiber 102.

The light L0 whose the polarization state has been adjusted by the polarization controller 103 is guided to the fiber coupler 105 through the optical fiber 104, and is split into the measurement light LS and the reference light LR.

The reference light LR is guided to the collimator 111 through the optical fiber 110 and becomes a parallel light beam. The reference light LR, which has become the parallel light beam, is guided to the corner cube 114 via an optical path length correction member 112 and a dispersion compensation member 113. The optical path length correction member 112 acts as a delay means for matching the optical path length (i.e., the optical distance) of the reference light LR and that of the measurement light LS. The dispersion compensation member 113 acts as a dispersion compensation means for matching the dispersion characteristic of the reference light LR and that of the measurement light LS.

The corner cube 114 changes the traveling direction of the reference light LR that has become a parallel light beam by the collimator 111 in the opposite direction. The optical path of the reference light LR incident on the corner cube 114 and the optical path of the reference light LR emitted from the corner cube 114 are parallel to each other. Further, the corner cube 114 is movable in a direction along the incident light path and the emitting light path of the reference light LR. Through such movement, the optical path length of the reference light LR (i.e., the reference optical path) is varied.

The reference light LR that has traveled through the corner cube 114 passes through the dispersion compensation member 113 and the optical path length correction member 112, is converted from the parallel light beam to the convergent light beam by a collimator 116, and enters an optical fiber 117. The reference light LR that has entered the optical fiber 117 is guided to the polarization controller 118. With the polarization controller 118, the polarization state of the reference light LR is adjusted.

The polarization controller 118 has the same configuration as, for example, the polarization controller 103. The reference light LR whose polarization state has been adjusted by the polarization controller 118 is guided to the attenuator 120 through the optical fiber 119, and the light amount of the reference light LR is adjusted under the control of the arithmetic control unit 200. The reference light LR whose light amount has been adjusted by the attenuator 120 is guided to the fiber coupler 122 through the optical fiber 121.

The measurement light LS generated by the fiber coupler 105 is guided through an optical fiber 127 and is collimated into a parallel light beam by the collimator lens unit 40. The measurement light LS made into a parallel light beam reaches the dichroic mirror 48 via the optical path length changing unit 41, the optical scanner 42, the collimate lens 43, the mirror 44, the OCT focusing lens 45, the field lens 46, and the VCC lens 47. Subsequently, the measurement light LS is reflected by the dichroic mirror 48, is refracted by the objective lens 22, and is projected onto the fundus Ef. The measurement light LS is scattered and reflected at various depth positions of the fundus Ef. Back-scattered light of the measurement light LS from the fundus Ef reversely advances along the same path as the outward path, and is guided to the fiber coupler 105. Then, the back-scattered light passes through an optical fiber 128, and arrives at the fiber coupler 122.

The fiber coupler 122 combines (interferes) the measurement light LS incident through the optical fiber 128 and the reference light LR incident through the optical fiber 121 to generate interference light. The fiber coupler 122 generates a pair of interference light LC by splitting the interference light generated from the measurement light LS and the reference light LR at a predetermined splitting ratio (for example, 1:1). The pair of the interference light LC emitted from the fiber coupler 122 is guided to the detector 125 through the optical fibers 123 and 124, respectively.

The detector 125 is, for example, a balanced photodiode that includes a pair of photodetectors for respectively detecting the pair of the interference light LC and outputs the difference between the pair of detection results obtained by the pair of photodetectors. The detector 125 sends the detection result (i.e., detection signal) to the arithmetic control unit 200. For example, the arithmetic control unit 200 performs the Fourier transform etc. on the spectral distribution based on the detection result obtained by the detector 125 for each series of wavelength scanning (i.e., for each A-line). With this, the tomographic image for each A-line is formed. The arithmetic control unit 200 displays the formed image on the display apparatus 3.

Although a Michelson interferometer is employed in the present embodiment, it is possible to employ any type of interferometer such as Mach-Zehnder-type as appropriate. In the present embodiment, in addition to the configuration shown in FIG. 2, the interference optical system may further include the collimator lens unit 40, the optical path length changing unit 41, the optical scanner 42, the collimate lens 43, the mirror 44, the OCT focusing lens 45, the field lens 46, and the VCC lens 47, which are shown in FIG. 1. This interference optical system is an example of the "interference optical system" according to the embodiments. The VCC lens 47 (and the VCC driver 47A) is an example of the "astigmatism correction optical member" according to the embodiments. The OCT focusing lens 45 (and the OCT focusing driver 45A) is an example of the "focusing position changing member" according to the embodiments. At least one of the optical path length changing unit 41 or the corner cube 114 (and the reference driver 114A) is an example of the "optical path length changing member" according to the embodiments. At least one of the polarization controller 103 or 118 is an example of the "polarization state changing member" according to the embodiments. The display controller 210 is an example of the "first display controller", the "second display controller", or the "third display controller" according to the embodiments.

[Arithmetic Control Unit 200]

The configuration of the arithmetic control unit 200 will be described.

Figure 4:
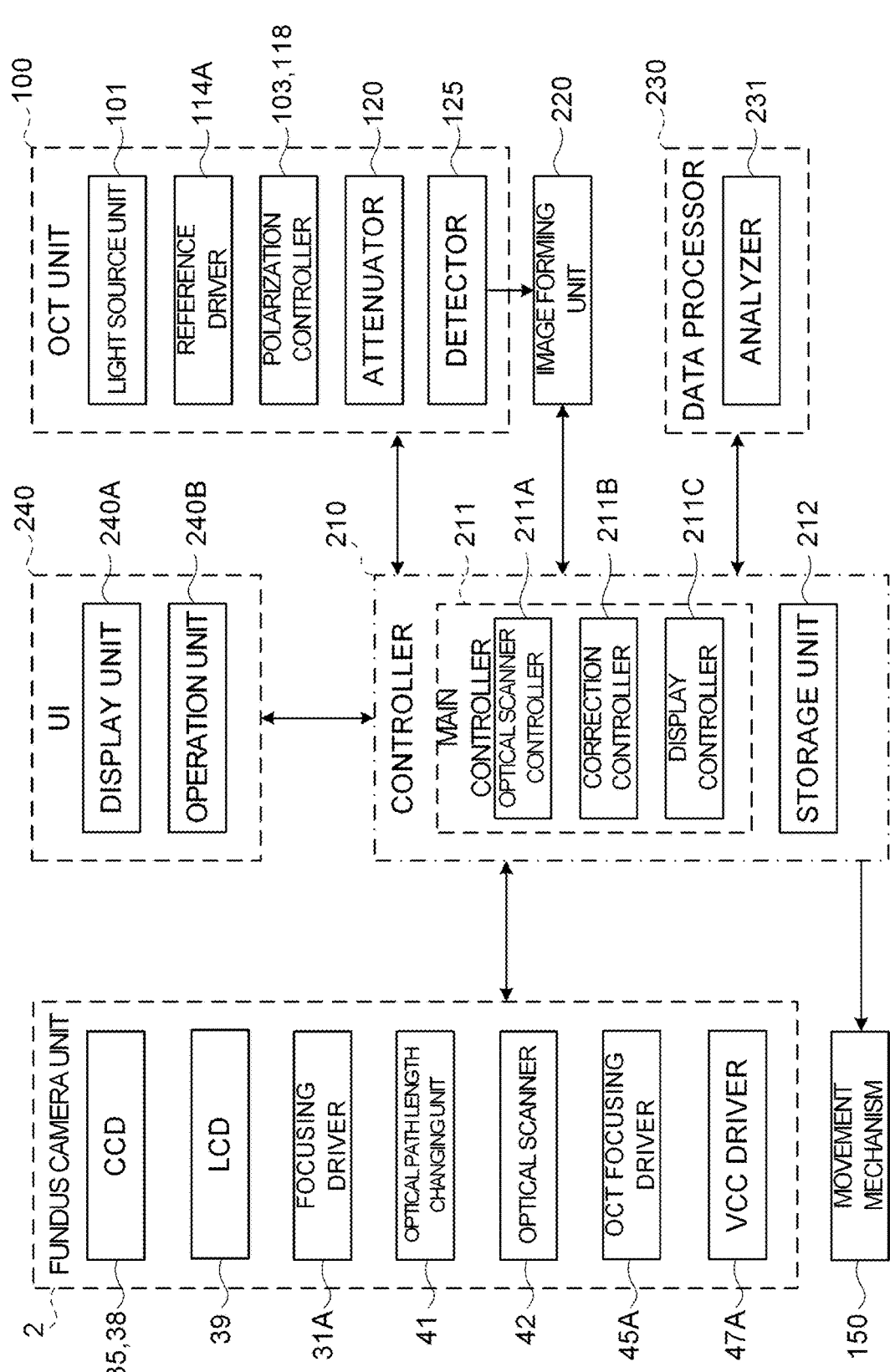
FIG. 4 is a schematic diagram illustrating an example of a configuration of a processing system of the ophthalmic apparatus according to the embodiments.
Figure 5:
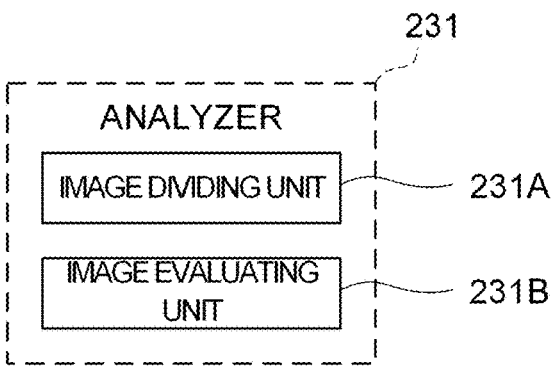
FIG. 5 is a schematic diagram illustrating an example of a configuration of a processing system of the ophthalmic apparatus according to the embodiments.

FIGS. 4 and 5 show block diagrams of examples of the configuration of the ophthalmic apparatus 1 according to the embodiments. FIG. 5 shows a functional block diagram representing an example of the configuration of an analyzer 231 in FIG. 4. In FIG. 4, like reference numerals designate like parts as in FIG. 1 or FIG. 2. The same description may not be repeated.

The arithmetic control unit 200 analyzes the detection signals fed from the detector 125 to form an OCT image of the fundus Ef. The arithmetic processing therefor is performed in the same manner as in the conventional swept source type OCT apparatus.

As shown in FIG. 4, the arithmetic control unit 200 includes a controller 210, and controls each part of the fundus camera unit 2, the display apparatus 3, and the OCT unit 100. For example, the arithmetic control unit 200 forms an OCT image (tomographic image, three-dimensional image) of the fundus Ef, and displays the formed OCT image on the display apparatus 3.

Examples of the control for the fundus camera unit 2 include the operation control for the observation light source 11, the operation control for the imaging light source 15 and the operation controls for the LEDs 51 and 61, the operation control for the LCD 39, the movement control for the focusing lens 31, the movement control for the OCT focusing lens 45, the movement control for the reflection rod 67, the movement control for the focus optical system 60, the movement control for the optical path length changing unit 41, the driving control for the VCC lens 47, and the operation control for the optical scanner 42.

Examples of the control for the OCT unit 100 include the operation control for the light source unit 101, the movement control for the corner cube 114, the operation control for the detector 125, the operation control for the attenuator 120, and the operation controls for the polarization controllers 103 and 118.

Like conventional computers, the arithmetic control unit 200 includes a microprocessor, a random access memory (RAM), a read only memory (ROM), a hard disk drive, a communication interface, and the like. A storage device such as the hard disk drive stores a computer program for controlling the ophthalmic apparatus 1. The arithmetic control unit 200 may include various kinds of circuitry such as a circuit board for forming OCT images. In addition, the arithmetic control unit 200 may include an operation device (or an input device) such as a keyboard and a mouse, and a display device such as an LCD.

The processor includes, for example, a circuit(s) such as, for example, a CPU (central processing unit), a GPU (graphics processing unit), an ASIC (application specific integrated circuit), and a PLD (programmable logic device). Examples of PLD include a simple programmable logic device (SPLD), a complex programmable logic device (CPLD), and a field programmable gate array (FPGA). The processor realizes, for example, the function according to the embodiments by reading out a computer program stored in a storage circuit or a storage device and executing the computer program. At least a part of the storage circuit or the storage apparatus may be included in the processor. Further, at least a part of the storage circuit or the storage apparatus may be provided outside of the processor. In some embodiments, the functions of the arithmetic control unit 200 are realized by one or more processors.

The fundus camera unit 2, the display apparatus 3, the OCT unit 100, and the arithmetic control unit 200 may be integrally provided (i.e., in a single housing), or they may be separately provided in two or more housings.

The controller 210 includes a main controller 211 and a storage unit 212.

(Main Controller 211)

The main controller 211 performs various controls by outputting control signals to each part of the ophthalmic apparatus 1 described above. In particular, the main controller 211 controls components of the fundus camera unit 2 such as the CCD image sensors 35 and 38, the LCD 39, the focusing driver 31A, the optical path length changing unit 41, the optical scanner 42, the OCT focusing driver 45A, and the VCC driver 47A. Further, the main controller 211 controls components of the OCT unit 100 such as the light source unit 101, the reference driver 114A, the polarization controllers 103 and 118, the attenuator 120, and the detector 125.

The main controller 211 controls an exposure time (charge accumulation time), a sensitivity, a frame rate, or the like of the CCD image sensor 35 or 38. In some embodiments, the main controller 211 controls the CCD image sensor 35 or 38 so as to acquire images having the desired image quality.

The main controller 211 performs display control of fixation targets or visual targets for the visual acuity measurement, for the LCD 39. Thereby, the visual target presented to the subject's eye E can be switched, or type of the visual targets can be changed. Further, the presentation position of the visual target to the subject's eye E can be changed by changing the display position of the visual target on the screen of the LCD 39.

The focusing driver 31A moves the focusing lens 31 in the optical axis direction. The main controller 211 controls the focusing driver 31A so that the focusing lens 31 is positioned at a desired focusing position. As a result, the focusing position of the imaging optical system 30 is changed.

For example, the main controller 211 analyzes the position of the split image in the light receiving image (split target) obtained by the CCD image sensor 35, and controls the focusing driver 31A and the focus optical system 60. Alternatively, for example, the main controller 211 controls the focusing driver 31A and the focus optical system 60. according to the operations performed by the user on the operation unit 240B described below, while displaying a live image of the subject's eye E on the display unit 240A described below.

The main controller 211 controls the optical path length changing unit 41 to change the optical path length of the reference light L S. Thereby, the difference between the optical path length of the measurement light LS and the optical path length of the reference light LR is changed.

For example, the main controller 211 analyzes the detection result of the interference light LC obtained by OCT measurement (or the OCT image formed based on the detection result), and controls the optical path length changing unit 41 so that the measurement site is positioned at a desired depth position.

The main controller 211 (optical scanner controller 211A described below) controls the optical scanner 42. The main controller 211 controls the optical scanner 42 so as to deflect the measurement light LS according to the deflection pattern corresponding to the scan mode set in advance.

Examples of scan mode like this include a line scan, a cross scan, a circle scan, a radial scan, a concentric scan, a multiline cross scan, a helical scan, a Lissajous scan, and a three-dimensional scan.

The line scan is a scan mode in which the measurement light LS is deflected so that the movement trajectory of the irradiated positions of the measurement light LS at the imaging site (measurement site) is line-shaped. The line direction of the movement trajectory can be changed (rotatable) around the optical axis on the xy-plane.

For example, the line scan includes a horizontal scan and a vertical scan. The horizontal scan is a scan mode in which measurement light LS is deflected so that the movement trajectory of the irradiated positions of the measurement light LS is in the horizontal direction (x direction). The horizontal scan also includes a mode in which the measurement light LS is deflected along a plurality of scan lines that are arranged in the vertical direction (y-direction) and extend in the horizontal direction. In this mode, the intervals between the scan lines may be set as desired. Further, the intervals between the scan lines may be set sufficiently small to form a three-dimensional image. Such a scan mode is referred to as three-dimensional scan. These items for the horizontal scan mode may be applied to the vertical scan mode in similar ways.

The cross scan is a scan mode in which the measurement light LS is deflected so that the movement trajectory of the irradiated positions of the measurement light LS at the imaging site (measurement site) is cross-shaped. For example, the cross scan can be performed by executing two line scans whose line directions cross each other. The angle at which the two line scans intersect can be changed. In some embodiments, the scan lengths in the B-scan direction of the two line scans are identical. In some embodiments, the scan lengths in the B-scan direction of the two line scans are different.

The circle scan is a scan mode in which the measurement light LS is deflected so that the movement trajectory of the irradiated positions of the measurement light LS at the imaging site (measurement site) is, for example, in a circle around the optical axis SO. For example, in the circle scan, the measurement light LS is deflected so that the movement trajectory is a perfect circle, ellipse, or arc (part of a circumference).

The radial scan is a scan mode in which the measurement light LS is deflected so that the movement trajectory of the irradiated positions of the measurement light LS at the imaging site (measurement site) is radial around the optical axis SO, for example. In the radial scan mode, the irradiated positions of the measurement light LS are moved along a radial trajectory consisting of a plurality of straight lines arranged via a predetermined angle. The cross scan described above is one mode of the radial scan.

For example, in the radial scan, two or more line scans with B-scan directions different from each other are performed. In some embodiments, the scan lengths in the B-scan direction of the two or more line scans are identical. In some embodiments, the scan length in the B-scan direction of at least one of the two or more line scans is different from the other scan lengths.

The concentric scan is a scan mode in which the measurement light LS is deflected so that the movement trajectory of the irradiated positions of the measurement light LS at the imaging site (measurement site) is concentric around the optical axis SO, for example. For example, in the concentric scan, the measurement light LS is deflected so that the movement trajectory of each circle is a perfect circle, ellipse, or arc (part of a circumference). In the concentric circle according to some embodiments, a plurality of circle scans with different diameters are performed in combination with each other. The circle scan is one mode of the concentric scan.

The multiline cross scan is a scan pattern in which a group of horizontal scan lines (for example, 5 lines) parallel to each other and a group of vertical scan lines (for example, 5 lines) parallel to each other are arranged so as to be perpendicular to each other in the vicinity of the center positions of the both groups of scan lines.

For example, in each group of scan lines in the multiline cross scan, two or more line scans are performed. In some embodiments, the scan lengths in the B-scan direction of the two or more line scans are identical. In some embodiments, the scan length in the B-scan direction of at least one of the two or more line scans is different from the other scan lengths.

The helical scan is a scan mode in which the measurement light LS is deflected so that the movement trajectory of the irradiated positions of the measurement light LS at the imaging site (measurement site) is helical around the optical axis SO, for example. In the helical scan mode, the irradiated positions of the measurement light LS are moved along a helical trajectory while the rotation radius is gradually reduced (or increased).

The Lissajous scan is a scan mode in which the measurement light LS is deflected so that the movement trajectory of the irradiated positions of the measurement light LS at the imaging site (measurement site) follows the Lissajous curve. The Lissajous scan is disclosed, for example, Japanese Unexamined Patent Application Publication No. 2018-68578.

Examples of scan mode, in which the measurement light LS is deflected in the horizontal and vertical directions on the plane perpendicular to the optical axis of the interference optical system among the scan modes described above, include the circle scan, the radial scan, the concentric scan, the multiline cross scan, the helical scan, the Lissajous scan, and the three-dimensional scan.

By scanning the imaging site with the measurement light LS according to the deflection pattern corresponding to the scan mode as described above, tomographic images can be acquired in the plane defined by the direction along the scan line (scan trajectory) and the direction of the fundus depth direction (z direction).

A region on the fundus Ef to be scanned with measurement light LS as described above, that is, a region on the fundus Ef subjected to OCT measurement, is referred to as a "scan region". For example, a scan region for the three-dimensional scan is a rectangular region in which a plurality of horizontal scans is arranged. For example, a scan region for the concentric scan is a disc-shaped region surrounded by the trajectory of circle scan with the largest diameter. In addition, a scan region for the radial scan is a disc-shaped (or polygonal) region formed by connecting the two end positions of each scan line.

The OCT focusing driver 45A moves the OCT focusing lens 45 along the optical axis SO of the measurement light LS. The main controller 211 controls the OCT focusing driver 45A so that the OCT focusing lens 45 is positioned at a desired focusing position. As a result, the focusing position of the measurement light LS is changed. The focusing position of the measurement light LS corresponds to the depth position (z position) of the beam waist of the measurement light LS.

For example, the main controller 211 controls the OCT focusing driver 45A based on a signal-to-noise ratio of the detection result of the interference light LC obtained by OCT measurement or evaluation value(s) (including statistical value of the evaluation values) corresponding to the image quality of the OCT image formed based on the detection result.

When a liquid crystal lens or an Alvarez lens is provided in place of the OCT focusing lens 45, the main controller 211 can control the liquid crystal lens or the Alvarez lens in the same way as it controls the OCT focusing driver 45A.

The VCC driver 47A rotates the cylindrical lenses 471 and 472 independently each other around the optical axis SO of the measurement light LS. Thereby, at least one of the cylindrical power or the cylindrical axis angle is changed.

For example, the main controller 211 controls the VCC driver 47A based on a signal-to-noise ratio of the detection result of the interference light LC obtained by OCT measurement or evaluation value(s) (including statistical value of the evaluation values) corresponding to the image quality of the OCT image formed based on the detection result. Specifically, the main controller 211 controls the VCC driver 47A based on a signal-to-noise ratio of the detection result of the interference light LC obtained by deflecting the measurement light LS according to the deflection pattern corresponding to the circle scan or evaluation value(s) (including statistical value of the evaluation values) corresponding to the image quality of the OCT image formed based on the detection result.

When a liquid crystal lens, a deformable mirror, or an Alvarez lens is provided in place of the VCC lens 47, the main controller 211 can control the liquid crystal lens, the deformable mirror, or the Alvarez lens in the same way as it controls the VCC driver 47A.

The main controller 211 controls the light source unit 101. The control for the light source unit 101 includes switching the light source on and off, controlling the intensity of the emitted light, changing the center frequency of the emitted light, changing the sweep speed of the emitted light, changing the sweep frequency, and changing the sweep wavelength range.

The reference driver 114A moves the corner cube 114 provided on the optical path of the reference light along this optical path. Thereby, the difference between the optical path length of the measurement light LS and the optical path length of the reference light LR is changed.

For example, the main controller 211 analyzes the detection result of the interference light LC obtained by OCT measurement (or the OCT image formed based on the detection result), and controls the reference driver 114A so that the measurement site is positioned at a desired depth position. In some embodiments, any one of the optical path length changing unit 41 and the reference driver 114A is provided.

The main controller 211 controls the polarization controllers 103 and 118. For example, the main controller 211 controls the polarization controllers 103 and 118 based on a signal-to-noise ratio of the detection result of the interference light LC obtained by OCT measurement or evaluation value(s) (including statistical value of the evaluation values) corresponding to the image quality of the OCT image formed based on the detection result.

The main controller 211 controls the attenuator 120. For example, the main controller 211 controls the attenuator 120 based on a signal-to-noise ratio of the detection result of the interference light LC obtained by OCT measurement or evaluation value(s) (including statistical value of the evaluation values) corresponding to the image quality of the OCT image formed based on the detection result.

The main controller 211 controls the detector 125. The control for the detector 125 includes the control for an exposure time (charge accumulation time), a sensitivity, a frame rate, or the like of the detector 125.

The movement mechanism 150 three-dimensionally moves the fundus camera unit 2 (OCT unit 100) relatively to the subject's eye E. For example, the main controller 211 is capable of controlling the movement mechanism 150 to three-dimensionally move the optical system installed in the fundus camera unit 2. This control is used for alignment and/or tracking. Here, the tracking is to move the optical system of the apparatus according to the movement of the subject's eye E. To perform tracking, alignment and focusing are performed in advance. The tracking is performed by moving the optical system of the apparatus in real time according to the position and orientation of the subject's eye E based on the image obtained by moving imaging the subject's eye E, thereby maintaining a suitable positional relationship in which alignment and focusing are adjusted.

In some embodiments, the main controller 211 (optical scanner controller 211A described below) corrects the position of scan range (second scan range) for OCT imaging, based on tracking information obtained by performing tracking (tracking information obtained by tracking the optical system (interference optical system) with respect to a movement of the subject's eye E). The main controller 211 can control the optical scanner 42 so as to scan the corrected scan range with the measurement light LS.

Further, the main controller 211 (display controller 211C described below) displays the various information on the display apparatus 3 (or display unit 240A described below). Examples of the information displayed on the display apparatus 3 include the results of imaging (observation image, OCT image (image of the subject's eye formed based on the detection result of the interference light LC obtained by scanning the second scan range with the measurement light LS), the measurement result (measured value), and the information representing the results of changes in imaging conditions described below.

In the present embodiment, a provisional imaging (provisional measurement) is performed before a main imaging (main measurement). Based on the detection result of the interference light LC acquired in the provisional imaging or the OCT image formed from the detection result, the imaging conditions for the main imaging are adjusted.

As shown in FIG. 4, the main controller 211 includes an optical scanner controller 211A, a correction controller 211B, and a display controller 211C.

The optical scanner controller 211A controls the optical scanner 42 so as to deflect the measurement light LS according to the deflection pattern corresponding to the scan mode set in advance, as described above. In the provisional imaging, the optical scanner controller 211A can control the optical scanner 42 in accordance with a scan mode different from the scan mode performed in the main imaging. For example, in the provisional imaging, the optical scanner controller 211A can control the optical scanner 42 so as to deflect the measurement light LS in a deflection direction different from the deflection direction of the measurement light LS in the main imaging. In some embodiments, the optical scanner controller 211A controls the optical scanner 42 in accordance with a scan mode different for each target to be adjusted, in the provisional imaging.

The correction controller 211B changes the imaging conditions by controlling each part of the ophthalmic apparatus 1 based on the detection result of the interference light LC or the OCT image formed from the detection result. The correction controller 211B changes the imaging conditions for OCT imaging by controlling at least one of the VCC lens 47, the optical path length changing unit 41, the reference driver 114A, the polarization controller 103, or the polarization controller 118.

The display controller 211C can display the results of the control by the correction controller 211B on the display apparatus 3, in addition to the display control for the display apparatus 3 as described above.

Further, the main controller 211 performs a process of writing data in the storage unit 212 and a process of reading out data from the storage unit 212.

(Storage Unit 212)

The storage unit 212 stores various types of data. Examples of the data stored in the storage unit 212 include image data of an OCT image, image data of a fundus image, and subject's eye information. The subject's eye information includes information on the subject such as patient ID and name, and information on the subject's eye such as identification information of the left eye/right eye. In addition, the storage unit 212 stores the optometric data obtained by an external device (e.g., a refractometer or subjective inspection apparatus) in advance, and various programs and data for operating the ophthalmic apparatus 1. The optometric data includes an astigmatic power of the subject's eye, and an astigmatic axis angle of the subject's eye. The optometric data may further include a spherical power of the subject's eye. The optometric data may include at least one of a spherical power of the subject's eye, an astigmatic power of the subject's eye, or an astigmatic axis angle of the subject's eye.

At least part of the above data stored in the storage unit 212 may be stored in a storage unit external to the ophthalmic apparatus 1. For example, the ophthalmic apparatus 1 is connected so as to be capable of communicating with a sever apparatus having a function of storing at least part of the above data via a network such as an in-hospital LAN (Local Area Network). Here, the ophthalmic apparatus 1 and the server apparatus are connected via a WAN (Wide Area Network) such as the Internet. Further, the ophthalmic apparatus 1 and the server apparatus may be connected via a network that combines the LAN and the WAN.

(Image Forming Unit 220)

An image forming unit 220 forms image data of a tomographic image of the fundus Ef based on the detection signal (interference signal) from the detector 125. That is, the image forming unit 220 forms the image data of the subject's eye E based on the detection result of the interference light LC obtained by the interference optical system. This processing includes processes such as noise removal (noise reduction), filter processing, and fast Fourier transform (FFT) in the same manner as the conventional swept source type OCT. The image data acquired in this manner is a data set including a group of image data formed by imaging the reflection intensity profiles of a plurality of A lines. Here, the A lines are the paths of the measurement light LS in the subject's eye E.

In order to improve the image quality, it is possible to repeatedly perform scan with the same pattern a plurality of times to collect a plurality of data sets, and to compose (i.e., average) the plurality of data sets.

The image forming unit 220 includes, for example, the circuitry described above. It should be noted that "image data" and an "image" based on the image data may not be distinguished from each other in the present specification. In addition, a site of the fundus Ef and an image of the site may not be distinguished from each other.

(Data Processor 230)

Data processor 230 performs various kinds of data processing (e.g., image processing) and various kinds of analysis on the detection result of the interference light LC or the image formed by the image forming unit 220. For example, the data processor 230 performs various correction processing, such as analysis processing of the signal-to-noise ratio of the interference signal, image brightness correction, dispersion correction, etc.

Further, the data processor 230 performs various kinds of image processing and various kinds of analysis processing on images captured by the fundus camera unit 2 (e.g., fundus images, anterior segment images, etc.).

The data processor 230 performs known image processing such as interpolation processing for interpolating pixels between tomographic images to form image data of the three-dimensional image of the fundus Ef. It should be noted that the image data of the three-dimensional image means image data in which the positions of pixels are defined in a three-dimensional coordinate system. Examples of the image data of the three-dimensional image include image data defined by voxels three-dimensionally arranged. Such image data is referred to as volume data or voxel data. To display an image based on volume data, the data processor 230 performs image rendering processing (e.g., volume rendering, maximum intensity projection (MIP)) on the volume data to form image data of a pseudo three-dimensional image taken from a specific view direction. The pseudo three-dimensional image is displayed on the display device such as the display unit 240A.

Further, stack data of a plurality of tomographic images may be formed as the image data of the three-dimensional image. The stack data is image data obtained by three-dimensionally arranging tomographic images along a plurality of scan lines based on positional relationship of the scan lines. That is, the stack data is image data obtained by representing tomographic images, which are originally defined in their respective two-dimensional coordinate systems, by a single three-dimensional coordinate system. That is, the stack data is image data formed by embedding tomographic images into a single three-dimensional space.

The data processor 230 can perform position matching between the fundus image and the OCT image. When the fundus image and the OCT image are obtained in parallel, the position matching between the fundus image and the OCT image, which have been (almost) simultaneously obtained, can be performed using the optical axis of the imaging optical system 30 as a reference. Such position matching can be achieved since the optical system for the fundus image and that for the OCT image are coaxial. Besides, regardless of the timing of obtaining the fundus image and the OCT image, position matching between the fundus image and the OCT image can be achieved by registering the fundus image with an image obtained by projecting the OCT image onto the xy plane. This position matching method can also be employed when the optical system for obtaining the fundus image and the optical system for OCT measurement are not coaxial. Further, when both the optical systems are not coaxial, if the relative positional relationship between these optical systems is known, the position matching can be performed with referring to the relative positional relationship in a manner similar to the case of coaxial optical systems.

(Analyzer 231)

The data processor 230 includes an analyzer 231 that performs analysis processing described above. The analyzer 231 analyzes at least the detection result of the interference light LC or the tomographic image formed by the image forming unit 220, and outputs evaluation value(s) (including statistical value(s) of the evaluation values) corresponding to the image quality (signal-to-noise ratio) of the tomographic image as the analysis result. The main controller 211 (correction controller 211B) can control at least one of the VCC lens 47, the OCT focusing driver 45A, the optical path length changing unit 41, the polarization controller 103, or the polarization controller 118, based on the analysis result obtained by the analyzer 231. In particular, the detection result of the interference light LC obtained by deflecting the measurement light LS according to the deflection pattern corresponding to the circle scan or the tomographic image formed based on the detection result is the target for the analysis performed by the analyzer. Thereby, the imaging conditions can be adjusted with high precision without being affected by the movement of the eyeball, etc., even when the speed of the light source has increased.

The analyzer 231 includes an image dividing unit 231A, and an image evaluating unit 231B, as shown in FIG. 5.

(Image Dividing Unit 231A)

The image dividing unit 231A generates a plurality of divided images by dividing the image formed by the image forming unit 220 in a direction intersecting an A-scan direction. In some embodiments, the image dividing unit 231A generates a plurality of divided images by dividing the tomographic image in the B scan direction (or a direction orthogonal to the A-scan direction). In some embodiments, the image dividing unit 231A generates a plurality of divided images by dividing in a direction intersecting the radial direction of the fan shape around the scan center position at a position corresponding to the pupil of the subject's eye E. The shapes or the sizes of the divided images may be the same or different.

Figure 6:
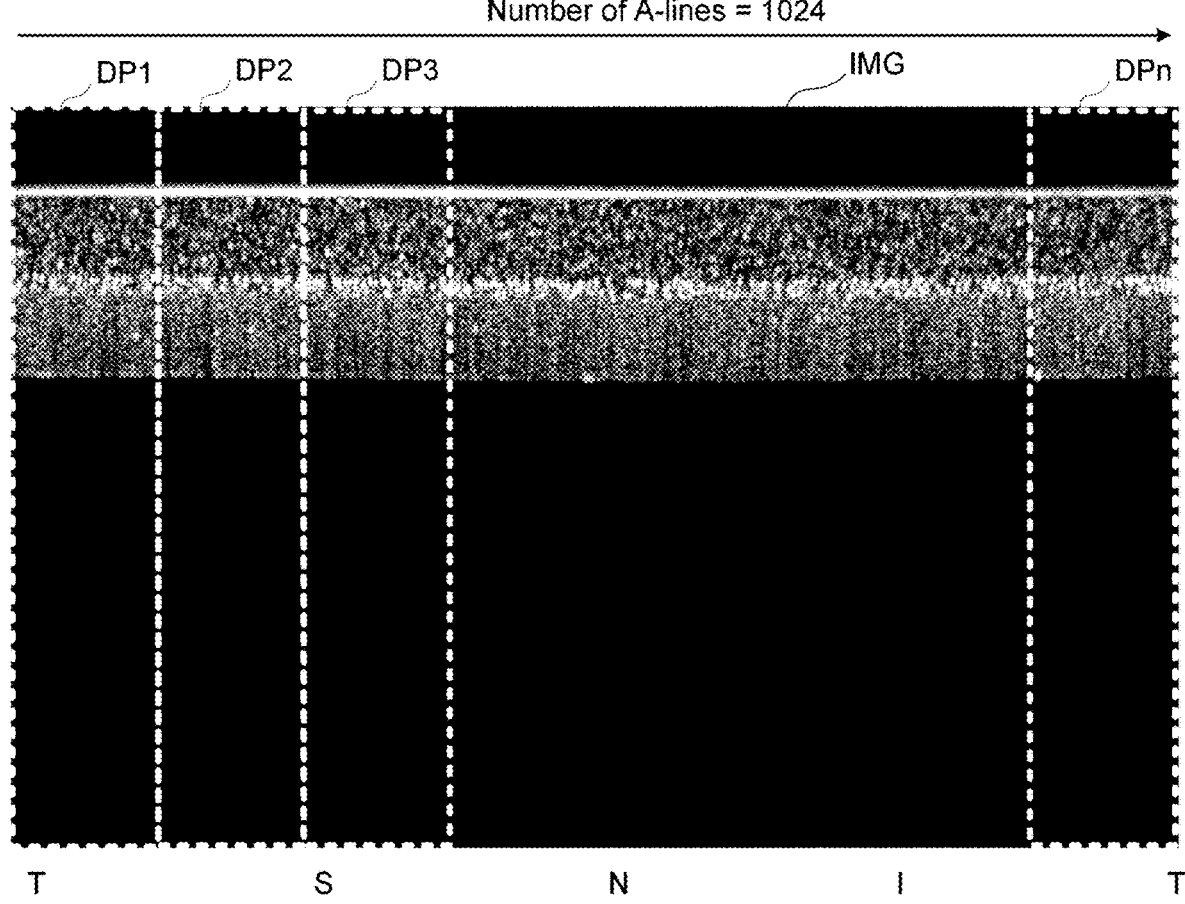
FIG. 6 is an explanatory diagram of an operation of the ophthalmic apparatus according to the embodiments.
Figure 7A:
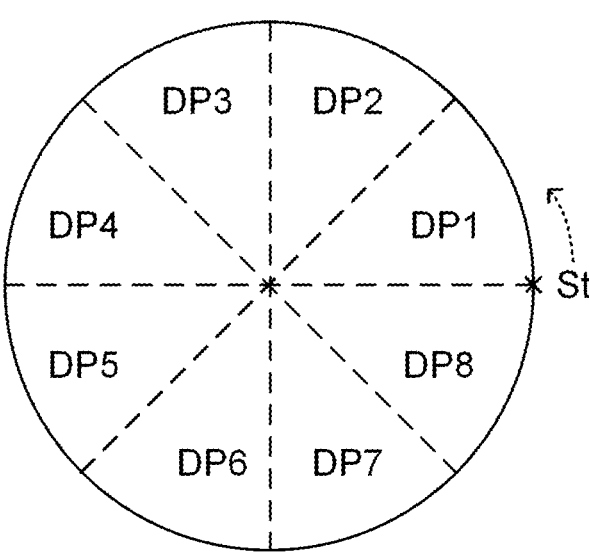
FIG. 7A is an explanatory diagram of an operation of the ophthalmic apparatus according to the embodiments.
Figure 7B:
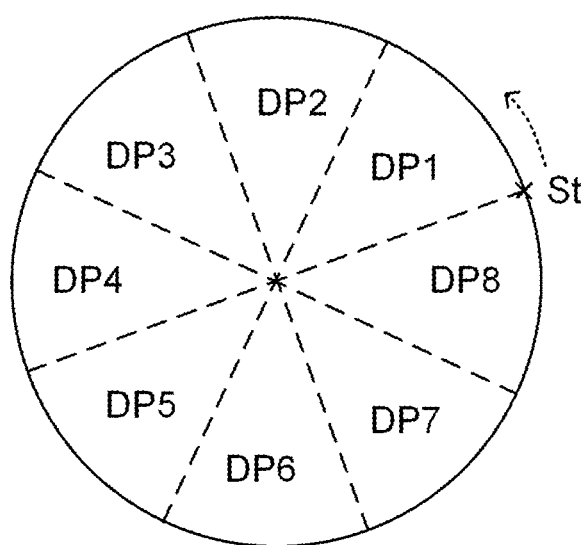
FIG. 7B is an explanatory diagram of an operation of the ophthalmic apparatus according to the embodiments.

FIG. 6, FIG. 7A, and FIG. 7B show diagrams describing the operation of the image dividing unit 231A according to the embodiments. FIG. 6 represents divided images DP1 to DPn obtained by dividing the tomographic image IMG obtained using the circle scan into n section(s) (n is 1 or more; n is 4 or more preferred). FIG. 7A and FIG. 7B schematically show an example in which the image dividing unit 231A divides the tomographic image obtained by performing the circle scan into 8 sections (segments). FIG. 7A and FIG. 7B schematically represent the movement trajectory of the irradiated positions the measurement light LS by the circle scan starting from the scan start position St.

In the tomographic image IMG, 1024 A-scan images are arranged in the B-scan direction (orthogonal to the A-scan direction). The image dividing unit 231A, for example, divides the tomographic image IMG in the B-scan direction into n sections, and generates the divided images DP1 to DPn. In FIG. 6, the divided images DP1 to DPn are generated in the circle scan direction moving in the order of temporal T, superior S, nasal N, inferior I, and temporal T. The width in the B-scan direction of each of the divided images DP1 to DPn may or may not be the same.

For example, in FIG. 7A, the tomographic image is divided so that the orientation of at least one of the boundaries of the divided images is in the horizontal direction (x direction) or the vertical direction (y direction). In contrast, in FIG. 7B, the tomographic image is divided so that the orientations of the boundaries of the divided images do not coincide in the horizontal and vertical directions. For example, by changing the scan start position St of the circle scan as shown in FIG. 7B, the tomographic image can be divided into 8 sections with reference to the A-scan line at the scan start position St. Alternatively, by changing the divided position of the tomographic image without changing the scan start position St, the tomographic image can be divided into 8 sections as shown in FIG. 7B.

As shown in FIG. 7B, by dividing the tomographic image so that the orientations of the boundaries of the divided images do not coincide in the horizontal and vertical directions, the sensitivity of the evaluation value to changes in image quality can be improved by taking advantage of the high probability of a large difference in image quality between the vertical and horizontal directions with respect to the astigmatic power and the astigmatic axis angle. Thereby, the imaging conditions can be adjusted with high precision.

In some embodiments, the image dividing unit 231A divides the tomographic image into an even number of sections. Thereby, the image evaluating unit 231B described below can evaluate the image quality based on the symmetry of the point-symmetric divided images with respect to the center position of the circle scan at the imaging site.

(Image Evaluating Unit 231B)

The image evaluating unit 231B performs analysis processing on each of the plurality of divided images generated by the image dividing unit 231A, and calculates evaluation values corresponding to the obtained analysis results. In other words, the image evaluating unit 231B calculates a plurality of evaluation values for the plurality of divided images.

The image evaluating unit 231B can calculate arbitrary evaluation values quantitatively representing the image quality. Typically, the evaluation values are calculated so that the higher the image quality, the larger the value. The calculation processing of the evaluation value performed by image evaluating unit 231B may be arbitrary processing. For example, the image evaluating unit 231B can perform processing using any known technology, such as the signal-to-noise ratio (SNR), the contrast-to-noise ratio (CNR), the root mean square (RMS) granularity, the Wiener spectrum, the modulation transfer function (MTF), the quality index (QI).

In some embodiments, the image evaluating unit 231B applies a predetermined analysis processing (e.g., segmentation processing) to an evaluation region set for an image corresponding to a predetermined site. Thereby, the image evaluating unit 231B identifies the image regions (signal regions) corresponding to the desired site (tissue) and other image regions (non-signal regions). Next, the image evaluating unit 231B generates a histogram of luminance in signal regions and a histogram of luminance in non-signal regions. Subsequently, the image evaluating unit 231B calculates the evaluation value corresponding to the image quality from the degree of overlap of these two histograms. For example, the evaluation value is defined in the range of 0 to 100, such that when both histograms completely overlap, the evaluation value=0, and when both histograms are completely separated, the evaluation value=100. This evaluation operation may include, for example, normalization of two histograms, generation of a probability distribution function, and calculation of the evaluation value using a predetermined arithmetic formula.

Further, the image evaluating unit 231B can calculate the statistical value of the plurality of evaluation values for the plurality of divided images. Examples of the statistical value include a maximum value, a minimum value, a median, an average value, a mode, a range, a variance, a standard deviation, and the value of a predetermined evaluation equation using any of the above statistics.

Examples of the evaluation equation include the following equation (1) such that the higher the total value of the evaluation values of the divided images and the smaller the variation of the evaluation values of the divided images, the larger the value VCCQ of the evaluation equation.

[Equation 1]

$$VCCQ = \frac{sum(IQ)}{stdevp(IQ)+1} = \frac{\sum_{i=1}^{n} IQ_i}{\sqrt{\frac{1}{n}\sum_{i=1}^{n}\left(IQ_i - \overline{IQ}\right)^2} + 1} \qquad (1)$$

In Equation (1), the value VCCQ of the evaluation equation is a value obtained by dividing the sum of the evaluation values of the plurality of divided images by (standard deviation of the plurality of evaluation values+1).

The main controller 211 (correction controller 211B) can control at least one of the VCC lens 47, the OCT focusing driver 45A, the optical path length changing unit 41, the polarization controller 103, or the polarization controller 118, based on the statistical value of the plurality of evaluation values calculated by the image evaluating unit 231B. For example, the control for the VCC lens 47, etc. and the OCT measurement are repeatedly performed so that the statistical value of the plurality of evaluation values is maximum (minimum, or a desired value).

In some embodiments, the main controller 211 controls at least one of the VCC lens 47, the OCT focusing driver 45A, the optical path length changing unit 41, the polarization controller 103, or the polarization controller 118, based on the value VCCQ of the evaluation equation obtained using the equation (1). In this case, the control for the VCC lens 47, etc. and the OCT measurement are repeatedly performed so that the value VCCQ of the evaluation equation is maximum.

The main controller 211 (display controller 211C) controls the display apparatus 3 or the display unit 240A (display means) to display the evaluation value(s) or the statistical value calculated by the image evaluating unit 231B. In some embodiments, the main controller 211 controls the display apparatus 3, etc. to display the evaluation values of the divided images, the evaluation values being associated with the divided images, for at least one of the divided images generated by the image dividing unit 231A.

The data processor 230 that functions described above includes, for example, a processor described above, a RAM, a ROM, a hard disk drive, a circuit board, and the like. Computer programs that cause a processor to execute the above functions are previously stored in a storage device such as a hard disk drive.

(User Interface 240)

The user interface 240 includes the display unit 240A and the operation unit 240B. The display unit 240A includes the display device of the arithmetic control unit 200 described above and/or the display apparatus 3. The operation unit 240B includes the operation device of the arithmetic control unit 200 described above. The operation unit 240B may include various kinds of buttons and keys provided on the housing of the ophthalmic apparatus 1, or provided outside the ophthalmic apparatus 1. For example, when the fundus camera unit 2 has a case similar to that of the conventional fundus camera, the operation unit 240B may include a joy stick, an operation panel, and the like provided to the case. Further, the display unit 240A may include various kinds of display devices, such as a touch panel placed on the housing of the fundus camera unit 2.

It should be noted that the display unit 240A and the operation unit 240B need not necessarily be formed as separate devices. For example, a device like a touch panel, which has a display function integrated with an operation function, can be used. In such cases, the operation unit 240B includes the touch panel and a computer program. The content of operation performed on the operation unit 240B is fed to the controller 210 as an electric signal. Moreover, operations and inputs of information may be performed using a graphical user interface (GUI) displayed on the display unit 240A and the operation unit 240B.

The display apparatus 3 or the display unit 240A is an example of the "display means" according to the embodiments.

<Example of Adjustment of Imaging Conditions>

As described above, in the present embodiment, the provisional imaging is performed before the main imaging, and the imaging conditions are adjusted for the main imaging. Examples of the adjustment of the imaging conditions include adjustment of the VCC lens 47, adjustment of the OCT focusing lens 45, adjustment of optical path length changing unit 41 or the corner cube 114, and adjustment of polarization controller 103 and 118.

(Example of Adjustment of VCC Lens 47)

First, the main controller 211 performs OCT measurement. In the OCT measurement, the circle scan is performed (that is, the measurement light LS is deflected in the horizontal and the vertical directions on the plane perpendicular to the optical axis of the interference optical system). The image forming unit 220 forms the tomographic image shown in FIG. 6, based on the detection result of the interference light LC obtained by performing the circle scan.

Next, the image dividing unit 231A divides the tomographic image to generate the plurality of divided images, as shown in FIG. 6. The image evaluating unit 231B calculated the evaluation values for each generated divided images, as described above. Subsequently, the image evaluating unit 231B calculates the statistical value of the plurality of evaluation values calculated for the plurality of divided images. For example, the image evaluating unit 231B calculates the value of the evaluation equation as shown in Equation (1) as the statistical value.

The main controller 211 controls the VCC driver 47A based on the statistical value of the plurality of evaluation values calculated by the image evaluating unit 231B. Thereby, at least one of the cylindrical power or the cylindrical axis angle is changed in accordance with the statistical value of the plurality of evaluation values of the plurality of divided images.

The main controller 211 iteratively performs (repeats) the OCT measurement, the calculation of the statistical value for the tomographic image based on the detection result of the interference light LC obtained by the OCT measurement, and the control for the VCC driver 47A, until the statistical value satisfies a predetermined first termination condition. The first termination condition is a condition for arranging a position of the circle of least confusion, which is equal to or smaller than the previously defined size, at a predetermined position. Here, the position of the circle of least confusion is an intermediate position between a position of the primary focal line, where the steeper meridian converges, and a position of the secondary focal line, where the flatter meridian converges. The predetermined position is a position at the fundus Ef (retina) or near the fundus Ef. For example, the main controller 211 iteratively performs the OCT measurement, the calculation of the statistical value, and the control for the VCC driver 47A so as to reduce the difference between the statistical value and a first previously defined value for satisfying the first termination condition. When the relationship between the statistical value and the first previously defined value becomes a predetermined first relationship, the main controller 211 terminates the adjustment of the VCC lens 47.

For example, the main controller 211 iteratively performs the OCT measurement, the calculation of the statistical value, and the control for the VCC driver 47A so that the sum of the evaluation values of the plurality of divided images becomes large and the variation of the evaluation values of the plurality of divided images becomes small.

In some embodiments, the display controller 211C displays at least one of the cylindrical power or the cylindrical axis angle before or after the change on the display apparatus 3 or the display unit 240A.

In some embodiments, the scan range of the circle scan performed in the above adjustment example is included in the imaging range for acquiring OCT images. That is, the optical scanner controller 211A controls the VCC lens 47 (VCC driver 47A) based on the detection result of the interference light LC obtained by interference optical system by controlling the optical scanner 42 so as to scan the first scan range of the subject's eye E with the measurement light LS. After that, the optical scanner controller 211A controls the optical scanner 42 so as to scan the second scan range including the first scan range with the measurement light LS. The image forming unit 220 forms the OCT image (tomographic image) of the subject's eye E based on the detection result of the interference light LC obtained by scanning the second scan range with the measurement light LS.

(Example of Adjustment of OCT Focusing Lens 45)

In some embodiments, the adjustment of the OCT focusing lens 45 is performed using the tomographic image (or the detection result of the interference light LC) obtained by performing the circle scan, as well as the adjustment of the VCC lens 47. In other words, the OCT measurement, the calculation of the statistical value described above, and the control for the OCT focusing driver 45A are iteratively performed, until the statistical value of the plurality of evaluation values of the plurality of divided images that is obtained by dividing the tomographic image acquired by performing the circle scan satisfies a predetermined second termination condition. The second termination condition may be the same as the first termination condition. For example, the main controller 211 iteratively performs the OCT measurement, the calculation of the statistical value, and the control for the OCT focusing driver 45A so as to reduce the difference between the statistical value and a second previously defined value for satisfying the second termination condition. When the relationship between the statistical value and the second previously defined value becomes a predetermined second relationship, the main controller 211 terminates the adjustment of the OCT focusing lens 45.

In some embodiments, the adjustment of the OCT focusing lens 45 is performed using the tomographic image (or the detection result of the interference light LC) obtained by performing scan other than the circle scan (for example, line scan). In other words, the OCT measurement, the calculation of the statistical value described above, and the control for the OCT focusing driver 45A are iteratively performed, until the statistical value of the plurality of evaluation values of the plurality of divided images that is obtained by dividing the tomographic image acquired by performing the line scan satisfies the predetermined second termination condition. The second termination condition may be the same as the first termination condition. For example, the main controller 211 iteratively performs the OCT measurement, the calculation of the statistical value, and the control for the OCT focusing driver 45A so as to reduce the difference between the statistical value and the second previously defined value for satisfying the second termination condition. When the relationship between the statistical value and the second previously defined value becomes a predetermined second relationship, the main controller 211 terminates the adjustment of the OCT focusing lens 45.

In some embodiments, the display controller 211C displays the position of the OCT focusing lens 45 before or after the change on the display apparatus 3 or the display unit 240A.

In some embodiments, the scan range of the scan performed in the above adjustment example is included in the imaging range for acquiring OCT images. That is, the optical scanner controller 211A controls the OCT focusing lens 45 (OCT focusing driver 45A) based on the detection result of the interference light LC obtained by interference optical system by controlling the optical scanner 42 so as to scan the first scan range of the subject's eye E with the measurement light LS. After that, the optical scanner controller 211A controls the optical scanner 42 so as to scan the second scan range including the first scan range with the measurement light LS. The image forming unit 220 forms the OCT image (tomographic image) of the subject's eye E based on the detection result of the interference light LC obtained by scanning the second scan range with the measurement light LS.

(Examples of Adjustment of Optical Path Length Changing Unit 41, Corner Cube 114)

In some embodiments, the adjustment of the optical path length changing unit 41 or the corner cube 114 is performed using the tomographic image (or the detection result of the interference light LC) obtained by performing the circle scan, as well as the adjustment of the VCC lens 47. In this case, the OCT measurement, the calculation of the evaluation value described above, and the control for the optical path length changing unit 41 or the reference driver 114A are iteratively performed, until a single evaluation value for the entire tomographic image obtained by performing the circle scan satisfies a predetermined third termination condition. The third termination condition is a condition for the image region corresponding to the site (tissue) of interest in the tomographic image to fall within a predetermined depth range. Identifying the image region corresponding to the site of interest in the tomographic image is performed by identifying a layer region corresponding to a desired site of interest from a plurality of layer regions obtained by performing segmentation processing on the tomographic image. For example, the main controller 211 iteratively performs the OCT measurement, the calculation of the evaluation value, and the control for the optical path length changing unit 41 or the corner cube 114 so as to reduce the difference between the evaluation value and a third previously defined value for satisfying the third termination condition. When the relationship between the evaluation value and the third previously defined value becomes a predetermined third relationship, the main controller 211 terminates the adjustment of the optical path length changing unit 41 or the corner cube 114.

In some embodiments, the adjustment of the optical path length changing unit 41 or the corner cube 114 is performed using the tomographic image (or the detection result of the interference light LC) obtained by performing the line scan. In this case, the OCT measurement, the calculation of the evaluation value described above, and the control for the optical path length changing unit 41 or the corner cube 114 are iteratively performed, until a single evaluation value for the entire tomographic image obtained by performing the line scan satisfies the predetermined third termination condition.

In some embodiments, the display controller 211C displays information corresponding to the optical path length before or after the change on the display apparatus 3 or the display unit 240A.

In some embodiments, the scan range of the scan performed in the above adjustment example is included in the imaging range for acquiring OCT images. That is, the optical scanner controller 211A controls the optical path length changing unit 41 or the corner cube 114 (reference driver 114A) based on the detection result of the interference light LC obtained by interference optical system by controlling the optical scanner 42 so as to scan the first scan range of the subject's eye E with the measurement light LS. After that, the optical scanner controller 211A controls the optical scanner 42 so as to scan the second scan range including the first scan range with the measurement light LS. The image forming unit 220 forms the OCT image (tomographic image) of the subject's eye E based on the detection result of the interference light LC obtained by scanning the second scan range with the measurement light LS.

(Example of Adjustment of Polarization Controllers 103 and 118)

In some embodiments, the adjustment of the polarization controllers 103 and 118 is performed using the tomographic image (or the detection result of the interference light LC) obtained by circle scan, as well as the adjustment of the VCC lens 47. In this case, the OCT measurement, the calculation of the evaluation value described above, and the control for the polarization controllers 103 and 118 are iteratively performed, until a single evaluation value for the entire tomographic image obtained by performing the circle scan satisfies a predetermined fourth termination condition. The fourth termination condition is a condition in which the image quality of the entire tomographic image is the highest (for example, the evaluation value becomes maximum value). For example, the main controller 211 iteratively performs the OCT measurement, the calculation of the statistical value, and the control for the polarization controllers 103 and 118 so as to reduce the difference between the evaluation value and a fourth previously defined value for satisfying the fourth termination condition. When the relationship between the evaluation value and the fourth previously defined value becomes a predetermined fourth relationship, the main controller 211 terminates the adjustment of the polarization controllers 103 and 118.

In some embodiments, the adjustment of the polarization controllers 103 and 118 is performed using the tomographic image (or the detection result of the interference light LC) obtained by performing the line scan. In this case, the OCT measurement, the calculation of the evaluation value described above, and the control for the polarization controllers 103 and 118 are iteratively performed, until the single evaluation value for the entire tomographic image obtained by performing the line scan satisfies the predetermined fourth termination condition.

In some embodiments, the display controller 211C displays information corresponding to the polarization state before or after the change on the display apparatus 3 or the display unit 240A.

In some embodiments, the scan range of the circle scan performed in the above adjustment example is included in the imaging range for acquiring OCT images. That is, the optical scanner controller 211A controls the polarization controllers 103 and 118 based on the detection result of the interference light LC obtained by interference optical system by controlling the optical scanner 42 so as to scan the first scan range of the subject's eye E with the measurement light LS. After that, the optical scanner controller 211A controls the optical scanner 42 so as to scan the second scan range including the first scan range with the measurement light LS. The image forming unit 220 forms the OCT image (tomographic image) of the subject's eye E based on the detection result of the interference light LC obtained by scanning the second scan range with the measurement light LS.

Figure 8A:
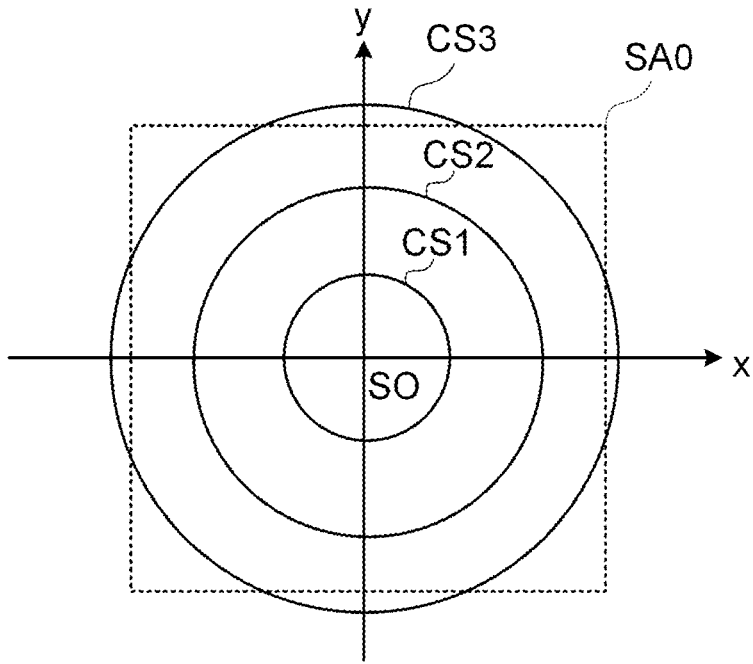
FIG. 8A is an explanatory diagram of an operation of the ophthalmic apparatus according to the embodiments.
Figure 8B:
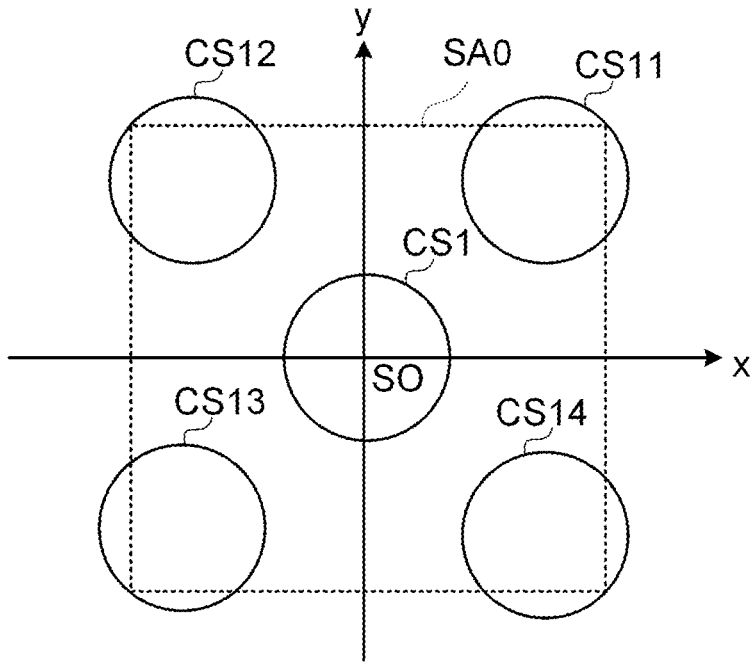
FIG. 8B is an explanatory diagram of an operation of the ophthalmic apparatus according to the embodiments.

FIG. 8A and FIG. 8B schematically show the scan ranges of the circle scan performed in the provisional imaging and the scan performed in the main imaging.

As shown in FIG. 8A, for the scan range SAO of the scan performed in the main imaging, for example, the circle scans CS1, CS2, and CS3 are performed in the provisional imaging. In other words, the circle scan(s) are/is performed to scan at least a part in the scan range SAO. The circle scan performed in provisional imaging is preferably encompassed within the scan range SAO (e.g., circle scans CS1 and CS2).

In some embodiments, as shown in FIG. 8B, the circle scans CS1, CS11, CS12, CS13, and CS14 so as to scan the center or corners of the scan range SAO. A circle scan may be performed by changing the position within the scan range SAO according to the object of the imaging conditions to be adjusted.

The spatial spread of the speckle noise of the laser beam (speckle size) is approximately equal to the diffraction limit r. The diffraction limit r is proportional to the center frequency $\lambda$ of the laser beam and inversely proportional to the numerical aperture of the objective lens 22. In some embodiments, when the number of A-lines in a circle-shaped scan line (diameter R) on the subject's eye E in case of performing the circle scan is N, $(R \times \pi / N) < r$ is satisfied. In this case, the number of A-lines in the circle scan can be reduced, and the imaging conditions can be adjusted more precisely in a shorter time.

It should be noted that in each of the above adjustment examples, the cases of forming the tomographic image have been described. However, it is also possible to calculate the evaluation value from the detection result of the interference light LC.

[Operation Example]

The operation of the ophthalmic apparatus 1 according to the embodiments will be described.

Figure 9:
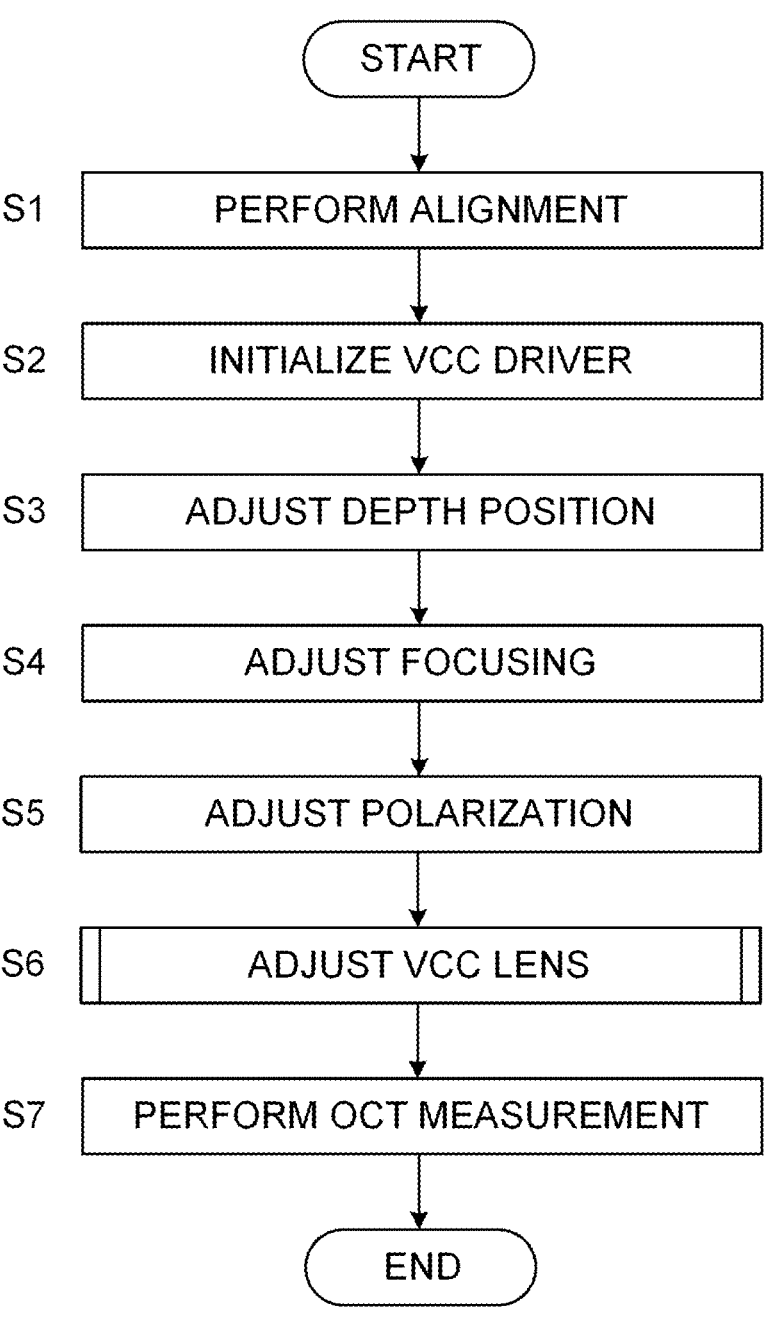
FIG. 9 is a flowchart illustrating an example of an operation of the ophthalmic apparatus according to the embodiments.
Figure 10A:
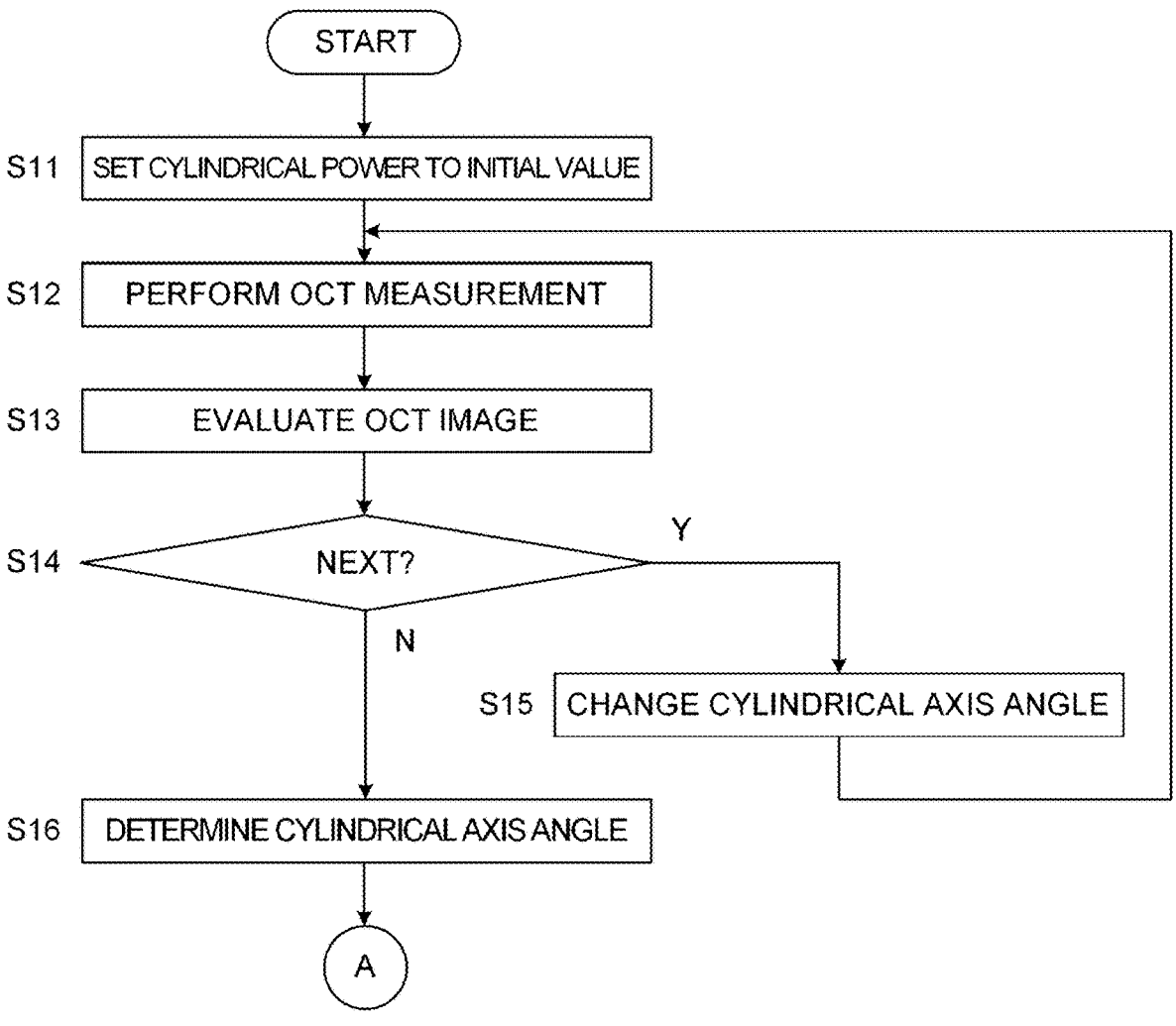
FIG. 10A is a flowchart illustrating an example of an operation of the ophthalmic apparatus according to the embodiments.
Figure 10B:
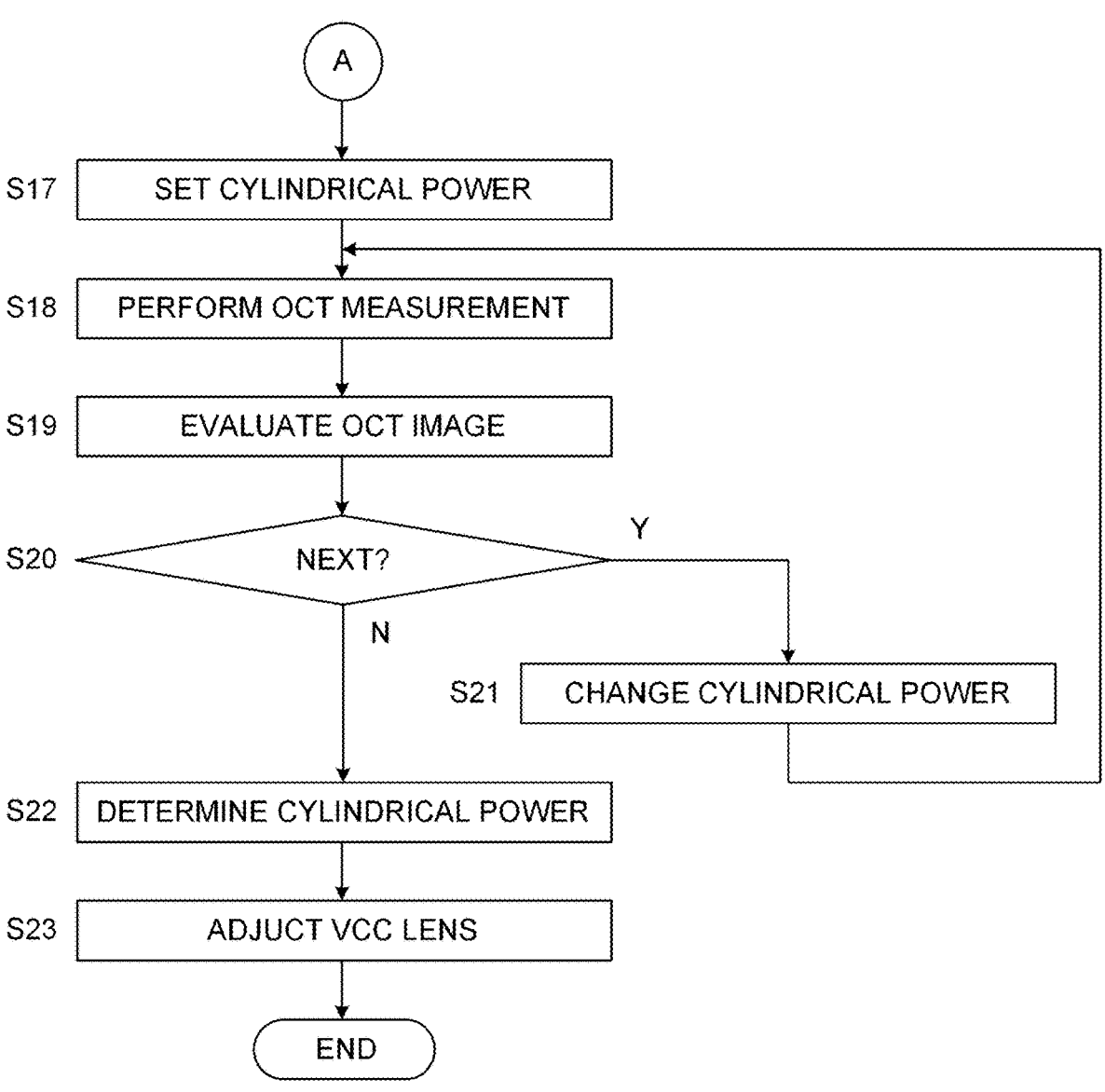
FIG. 10B is a flowchart illustrating an example of an operation of the ophthalmic apparatus according to the embodiments.

FIG. 9, FIG. 10A, and FIG. 10B show flowcharts of examples of the operation of the ophthalmic apparatus 1 according to the embodiments. FIG. 9 shows a flowchart of the operation example of the ophthalmic apparatus 1 according to the embodiments. FIG. 10A and FIG. 10B show flowcharts of examples of the operation of step S6 in FIG. 9. The storage unit 212 stores computer program(s) for realizing the processing shown in FIG. 9, FIG. 10A, and FIG. 10B. The main controller 211 operates according to the computer programs, and thereby the main controller 211 performs the processing shown in FIG. 9, FIG. 10A, and FIG. 10B.

(S1: Perform Alignment)

First, the main controller 211 performs alignment adjustment of the optical system relative to the subject's eye E in a state where the fixation target is presented at a predetermined fixation position. Examples of the alignment adjustment include manual alignment and automatic alignment.

When the alignment adjustment is performed manually, the main controller 211 controls the alignment optical system 50 to project a pair of alignment indicators onto the subject's eye E. A pair of alignment bright spots are displayed on the display unit 240A as the light receiving images of these alignment indicators. Further, the main controller 211 displays an alignment scale representing the target position of movement of the pair of alignment bright spots on the display unit 240A. The alignment scale is, for example, a bracket type image.

When the positional relationship between the subject's eye E and the fundus camera unit 2 (objective lens 22) is appropriate, that is, when the distance (working distance) between the subject's eye B and the fundus camera unit 2 is appropriate and the optical axis of the optical system of the fundus camera unit 2 and the ocular axis (corneal apex position) of the subject's eye E are (approximately) coincident, the pair of alignment bright spots are formed at a predetermined position (for example, intermediate position between the corneal apex and the center of corneal curvature) respectively, and is projected onto the subject's eye E, according to a known method. The examiner (user) can perform the alignment adjustment of the optical system to the subject's eye E by moving the fundus camera unit 2 three-dimensionally so as to guide the pair of alignment bright spots into the alignment scale.

When the alignment adjustment is performed automatically, the movement mechanism 150 for moving the fundus camera unit 2 is used. The data processor 230 identifies the position of each alignment bright spot in the screen displayed on display unit 240A, and obtains a displacement between the identified position of each alignment bright point and the alignment scale. The main controller 211 controls the movement mechanism 150 to move the fundus camera unit 2 so as to cancel this displacement. Identifying the position of each alignment bright spot can be performed, for example, by obtaining the luminance distribution of each alignment bright spot and obtaining the position of the center of gravity based on this luminance distribution. Since the position of the alignment scale is constant, the desired displacement can be obtained, for example, by calculating the displacement between the center position of the alignment scale and the above position of the center of gravity. The movement direction and the movement distance of the fundus camera unit 2 can be determined by referring to a preset unit movement distances in the x direction, y direction, and z direction (e.g., the result of prior measurement of how much the alignment indicator moves in which direction, when the fundus camera unit 2 is moved by how much in which direction). The main controller 211 generates signals according to the determined movement direction and movement distance, and transmits these signals to the movement mechanism 150. Thereby, the position of the optical system relative to the subject's eye E is changed automatically.

(S2: Initialize VCC Driver)

Next, the main controller 211 initializes the VCC driver 47A. By initializing the VCC driver 47A, the cylindrical power of the VCC lens 47 is initialized. This avoids a situation in which each part of the ophthalmic apparatus 1 is adjusted with an unintended cylindrical power applied in steps S3 to S6 described below.

(S3: Adjust Depth Position)

Subsequently, the main controller 211 performs adjustment of the depth position at which the image region corresponding to the site of interest is drawn so that the image region corresponding to the site of interest in the subject's eye E falls within a predetermined depth range in the tomographic image.

Specifically, the main controller 211 turns the light source unit 101 on and controls the optical scanner 42 so as to deflect the measurement light LS according to the deflection pattern corresponding to the line scan to perform OCT measurement.

Next, the main controller 211 controls the image forming unit 220 to form the tomographic image based on the detection result of the interference light LC acquired by performing the line scan.

Next, the main controller 211 controls the analyzer 231 to perform segmentation processing on the tomographic image to identify a plurality of layer regions. The analyzer 231 identifies a first layer region on a desired shallow layer side and a second layer region on a deep layer side, from the identified plurality of layer regions. The main controller 211 controls the optical path length changing unit 41 or the reference driver 114A so that the image region corresponding to a region between the identified first layer region and the identified second layer region falls within the predetermined depth range in the tomographic image.

In some embodiments, in step S3, the line scan and the identification processing of the layer region are repeated so that the image region corresponding to the region between the first layer region and the second layer region falls within the desired depth range in the tomographic image.

In some embodiments, in step S3, the detection result of the interference light LC is obtained by performing the circle scan.

(S4: Adjust Focusing)

Next, the main controller 211 performs adjustment of focusing.

Specifically, the main controller 211 turns the light source unit 101 on and controls the optical scanner 42 so as to deflect the measurement light LS according to the deflection pattern corresponding to the circle scan to perform OCT measurement.

Next, the main controller 211 controls the image forming unit 220 to form the tomographic image based on the detection result of the interference light LC acquired by performing the circle scan.

Subsequently, the main controller 211 controls the image dividing unit 231A to generate a plurality of divided images by dividing the formed tomographic image in the B-scan direction. The image dividing unit 231A, generates the divided images DP1 to DP8 by dividing the tomographic image in the B-scan direction into 8 sections, for example.

Next, the main controller 211 controls the image evaluating unit 231B to calculate the evaluation value corresponding to the image quality of each of the generated divided images DP1 to DP8. The image evaluating unit 231B calculates the evaluation value for each generated divided image, as described above. Further, the image evaluating unit 231B calculates the statistical value of the plurality of evaluation values calculated for the plurality of divided images. The image evaluating unit 231B calculates the value VCCQ of the evaluation equation shown in Equation (1) as the statistical value, for example.

The main controller 211 controls the OCT focusing driver 45A based on the statistical value (value VCCQ of the evaluation equation) of the plurality of evaluation values calculated by the image evaluating unit 231B. Thereby, the OCT focusing lens 45 is moved to a position corresponding to the statistical value of the plurality of evaluation values.

Until the statistical value of the plurality of evaluation values satisfies a predetermined termination condition, the OCT measurement, the calculation of the statistical value described above, and the control for the OCT focusing driver 45A are iteratively performed. For example, the main controller 211 iteratively performs the OCT measurement, the calculation of the statistical value, and the control for the OCT focusing driver 45A so as to reduce the difference between the statistical value and a previously defined value for satisfying the termination condition. When the relationship between the statistical value and the previously defined value becomes a predetermined relationship, the main controller 211 terminates the adjustment of the OCT focusing lens 45.

(S5: Adjust Polarization)

Next, the main controller 211 performs adjustment of the polarization. In the adjustment of the polarization, at least one of the polarization state of the measurement light LS or the polarization state of the reference light LR is adjusted.

Specifically, the main controller 211 turns the light source unit 101 on and controls the optical scanner 42 so as to deflect the measurement light LS according to the deflection pattern corresponding to the circle scan to perform OCT measurement.

Next, the main controller 211 controls the image forming unit 220 to form the tomographic image based on the detection result of the interference light LC acquired by performing the circle scan.

Subsequently, the main controller 211 controls the image dividing unit 231A to generate a plurality of divided images by dividing the formed tomographic image in the B-scan direction. The image dividing unit 231A, generates the divided images DP1 to DP8 by dividing the tomographic image in the B-scan direction into 8 sections, for example.

Next, the main controller 211 controls the image evaluating unit 231B to calculate the evaluation value corresponding to the image quality of each of the generated divided images DP1 to DP8. The image evaluating unit 231B calculates the evaluation values for each generated divided image, as described above. Further, the image evaluating unit 231B calculates the statistical value of the plurality of evaluation values calculated for the plurality of divided images. The image evaluating unit 231B calculates the value VCCQ of the evaluation equation shown in Equation (1) as the statistical value, for example.

The main controller 211 controls the polarization controller 103 or the polarization controller 118 so that the statistical value (value VCCQ of the evaluation equation) of the plurality of evaluation values calculated by the image evaluating unit 231B becomes maximum. Thereby, at least one of the polarization state of the measurement light LS or the polarization state of the reference light LR is changed in accordance with the statistical value of the plurality of evaluation values. In some embodiments, after one of the polarization controller 103 and the polarization controller 118 is adjusted, the other is adjusted.

Until the statistical value of the plurality of evaluation values satisfies a predetermined termination condition, the OCT measurement, the calculation of the statistical value described above, and the control for the polarization controllers 103 and 118 are iteratively performed. For example, the main controller 211 iteratively performs the OCT measurement, the calculation of the statistical value, and the control for the polarization controllers 103 and 118 so as to reduce the difference between the statistical value and a previously defined value for satisfying the predetermined termination condition. When the relationship between the statistical value and the previously defined value becomes a predetermined relationship, the main controller 211 terminates the adjustment of the polarization controllers 103 and 118.

(S6: Adjust VCC Lens)

The main controller 211 performs adjustment of the VCC lens 47.

The details of step S6 will be described below.

(S7: Perform OCT Measurement)

Once the imaging conditions are adjusted by adjusting each part of the ophthalmic apparatus 1 in steps S2 to S6, the main controller 211 performs the OCT measurement for the main imaging.

Specifically, the main controller 211 turns the light source unit 101 on and controls the optical scanner 42 so as to deflect the measurement light LS according to the deflection pattern corresponding to a desired scan mode to perform OCT measurement. In step S7, for example, the line scan, the circle scan, the radial scan, the multiline cross scan, or the 3D scan is performed.

Next, the main controller 211 controls the image forming unit 220 to form the tomographic image based on the detection result of the interference light LC acquired by performing scan with the deflection pattern corresponding to the desired scan mode.

In step S7, the formed tomographic image is used to display a live image of the subject's eye E, or a three-dimensional image is formed.

This terminates the operation of the ophthalmic apparatus 1 (END).

In step S6 in FIG. 9, for example, the flows shown in FIG. 10A and FIG. 10B are performed.

Figure 11:
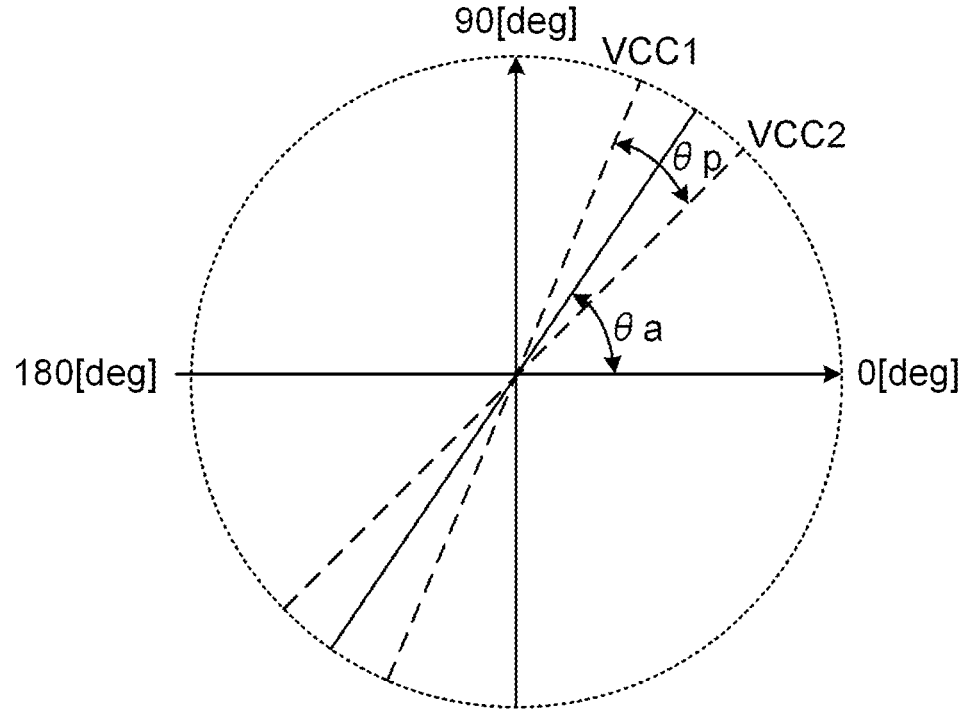
FIG. 11 is an explanatory diagram of an operation of the ophthalmic apparatus according to the embodiments.

FIG. 11 shows a diagram for explaining the operation of step S6 in FIG. 9. FIG. 11 schematically represents the axial direction of the cylindrical lens 471 (VCC1) and the axial direction of the cylindrical lens 472 (VCC2). In FIG. 11, for convenience of explanation, the axis angle in the horizontal direction is represented as 0 degrees, the axis angle in the vertical (upward) direction is represented as 90 degrees, and the rotation direction toward 90 degrees from 0 degrees is the positive direction.

(S11: Set Cylindrical Power to Initial Value)

First, the main controller 211 controls the VCC driver 47A to set the cylindrical power (Op in FIG. 11) to the initial value by rotating the cylindrical lenses 471 and 472.

Specifically, the main controller 211 controls the VCC driver 47A to set the axial direction of the cylindrical lens 471 and the axial direction of the cylindrical lens 472 to 0 degrees. After that, the main controller 211 controls the VCC driver 47A to change the axial direction of the cylindrical lens 471 and the axial direction of the cylindrical lens 472, and set the cylindrical power $\theta p$ to $\theta p'$ ($\theta p = \theta p'$).

Subsequently, the main controller 211 performs the control for determining the cylindrical axis angle of the VCC lens 47 (steps S12 to S16).

(S12: Perform OCT Measurement)

Next, the main controller 211 controls the OCT unit 100, etc. to perform OCT measurement.

Specifically, the main controller 211 turns the light source unit 101 on and controls the optical scanner 42 so as to deflect the measurement light LS according to the deflection pattern corresponding to the circle scan to perform OCT measurement.

(S13: Evaluate OCT Image)

Next, the main controller 211 controls the image forming unit 220 to form the OCT image of the subject's eye E based on the detection result of the interference light LC acquired in step S12.

Subsequently, the main controller 211 controls the image dividing unit 231A to generate the divided images DP1 to DP8 by dividing the formed OCT image in the B-scan direction.

Subsequently, the main controller 211 controls the image evaluating unit 231B to calculate the evaluation value corresponding to the image quality of each of the generated divided images DP1 to DP8. The image evaluating unit 231B calculates the evaluation value for each generated divided image, as described above. Further, the image evaluating unit 231B calculates the statistical value of the evaluation values calculated for the divided images DP1 to DP8. The image evaluating unit 231B calculates the value VCCQ of the evaluation equation shown in Equation (1) as the statistical value, for example.

(S14: Next?)

Next, the main controller 211 further changes the cylindrical axis angle and determines whether or not to re-evaluate the OCT image. For example, the main controller 211 repeats the re-evaluation of the OCT image so that the OCT image is evaluated for the cylindrical axis angle $\theta a$ in the range from 0 to 180 degrees.

When it is determined in step S14 that the OCT image is to be re-evaluated (step S14: Y), the operation of the ophthalmic apparatus 1 proceeds to step S15. On the other hand, when it is determined that the OCT image is not to be re-evaluated in step S14 (step S14: N), the operation of the ophthalmic apparatus 1 proceeds to step S16.

(S15: Change Cylindrical Axis Angle)

When it is determined in step S14 that the OCT image is to be re-evaluated (step S14: Y), the main controller 211 controls the VCC driver 47A to change the axis direction of the cylindrical lens 471 and the axis direction of the cylindrical lens 472 while maintaining the cylindrical power $\theta p$.

Specifically, the main controller 211 controls the VCC driver 47A to change the cylindrical axis angle in the positive direction by a predetermined step.

The operation of the ophthalmic apparatus 1 proceeds to step S12.

Steps S12 to S15 are repeatedly performed for the cylindrical axis angle $\theta a$ ranging from 0 to 180 degrees.

(S16: Determine Cylindrical Axis Angle)

When it is determined in step S14 that the OCT image is not to be re-evaluated (step S14: N), the main controller 211 determines the cylindrical axis angle.

Specifically, the main controller 211 identifies the maximum value of the statistical value calculated in step S13, which is performed repeatedly for the cylindrical axis angle $\theta a$ ranging from 0 to 180 degrees, and identifies the cylindrical axis angle $\theta a'$ when the statistical value is the maximum value. The main controller 211 determines the identified cylindrical axis angle as the cylindrical axis angle $\theta a$ ($\theta a = \theta a'$).

Subsequently, the main controller 211 performs the control for determining the cylindrical power of the VCC lens 47 (steps S17 to S22).

(S17: Set Cylindrical Power)

Next, the main controller 211 controls the VCC driver 47A to set the cylindrical power by rotating the cylindrical lenses 471 and 472.

For example, the main controller 211 controls the VCC driver 47A to rotate the cylindrical lens 471 by $+\theta p'/2$ and to rotate the cylindrical lens 472 by $-\theta p'/2$. Thereby, the cylindrical axis angle $\theta a1$ of the cylindrical lens 471 (VCC1) is expressed as in Equation (2).

[Equation 2]

$$\theta a1 = \theta a' + \frac{\theta p'}{2} \qquad (2)$$

Similarly, the cylindrical axis angle $\theta a2$ of the cylindrical lens 472 (VCC2) is expressed as in Equation (3).

[Equation 3]

$$\theta a2 = \theta a' - \frac{\theta p'}{2} \qquad (3)$$

As shown in FIG. 11, the cylindrical power $\theta p$ is determined by the angle formed by the cylindrical axis angles $\theta a1$ and $\theta a2$.

(S18: Perform OCT Measurement)

Next, the main controller 211 controls the OCT unit 100, etc. to perform OCT measurement, in the same manner as step S12.

(S19: Evaluate OCT Image)

Next, the main controller 211 controls the image forming unit 220 to form the OCT image of the subject's eye E based on the detection result of the interference light LC acquired in step S18, in the same manner as step S13.

Subsequently, the main controller 211 controls the image dividing unit 231A to generate the divided images DP1 to DP8 by dividing the formed OCT image in the B-scan direction.

Subsequently, the main controller 211 controls the image evaluating unit 231B to calculate the evaluation value corresponding to the image quality of each of the generated divided images DP1 to DP8. The image evaluating unit 231B calculates the evaluation value for each generated divided image, as described above. Further, the image evaluating unit 231B calculates the statistical value of the evaluation values calculated for the divided images DP1 to DP8. The image evaluating unit 231B calculates the value VCCQ of the evaluation equation shown in Equation (1) as the statistical value, for example.

(S20: Next?)

Next, the main controller 211 further changes the cylindrical power and determines whether or not to re-evaluate the OCT image. For example, the main controller 211 repeats the re-evaluation of the OCT image so that the OCT image is evaluated for the cylindrical power $\theta p$ in the range from 0 to 90 degrees.

When it is determined in step S20 that the OCT image is to be re-evaluated (step S20: Y), the operation of the ophthalmic apparatus 1 proceeds to step S21. On the other hand, when it is determined in step S20 that the OCT image is not to be re-evaluated (step S20: N), the operation of the ophthalmic apparatus 1 proceeds to step S22.

(S21: Change Cylindrical Power)

When it is determined in step S20 that the OCT image is to be re-evaluated (step S20: Y), the main controller 211 controls the VCC driver 47A to change the axis direction of the cylindrical lens 471 and the axis direction of the cylindrical lens 472 while maintaining the cylindrical axis angle $\theta a$.

Specifically, the main controller 211 controls the VCC driver 47A to change the cylindrical power by a predetermined step by changing at least one of the axial direction of the cylindrical lens 471 or the axial direction of the cylindrical lens 472.

The operation of the ophthalmic apparatus 1 proceeds to step S18.

Steps S18 to S21 are repeatedly performed for the cylindrical power $\theta p$ ranging from 0 to 90 degrees.

(S22: Determined Cylindrical Power)

When it is determined in step S20 that the OCT image is not to be re-evaluated (step S20: N), the main controller 211 determines the cylindrical power.

Specifically, the main controller 211 identifies the maximum value of the statistical value calculated in step S19, which is performed repeatedly for the cylindrical power $\theta p$ ranging from 0 to 90 degrees, and identifies the cylindrical power $\theta p''$ when the statistical value is the maximum value. The main controller 211 determines the identified cylindrical power as the cylindrical power $\theta p$ ($\theta p = \theta p''$).

(S23: Adjust VCC Lens)

Subsequently, the main controller 211 controls the VCC driver 47A to adjust VCC lens 47 using the cylindrical axis angle $\theta a'$ determined in step S16 and the cylindrical power $\theta p''$ determined in step S22.

Specifically, the main controller 211 controls the VCC driver 47A to set the cylindrical axis angle $\theta a1$ of the cylindrical lens 471 as shown in Equation (4).

[Equation 4]

$$\theta a1 = \theta a' + \frac{\theta p''}{2} \qquad (4)$$

In the same way, the main controller 211 controls the VCC driver 47A to set the cylindrical axis angle $\theta a2$ of the cylindrical lens 472 as shown in Equation (5).

[Equation 5]

$$\theta a2 = \theta a' - \frac{\theta p''}{2} \qquad (5)$$

This terminates the processing of step S6 in FIG. 9 (END).

As described above, since the circle scan is used to adjust at least the VCC lens 47, the information in the horizontal direction and the information in the vertical direction on the plane perpendicular to the optical axis of the interference optical system can be acquired in a shorter time than the time required for raster scan (or two or more line scans). Therefore, the information in the horizontal direction and the information in the vertical direction can be acquired, and the astigmatism can be corrected from the acquired the information in the horizontal direction and the acquired information in the vertical direction. As a result, the astigmatism can be corrected with high precision without being affected by eye movement or other factors, even when the speed of the light source is increased.

Further, since the scan mode is changed for each target to be adjusted determining the imaging conditions, it is possible to change the imaging conditions in the optimal scan mode in accordance with the target to be adjusted. This allows to adjust the imaging conditions in a shorter time with high precision.

It should be noted that the order of steps in FIG. 9 is not limited. For example, the order performing each step in steps S4 to S6 can be changed arbitrarily.

In some embodiments, a program for causing a computer to execute the method of controlling the ophthalmic apparatus described above is provided. Such a program can be stored in any non-transitory computer-readable recording medium. The recording medium may be an electronic medium using magnetism, light, magneto-optical, semiconductor, or the like. Typically, the recording medium is a magnetic tape, a magnetic disk, an optical disk, a magneto-optical disk, a flash memory, a solid state drive, or the like. The computer program may be transmitted and received through a network such as the Internet, LAN, etc.

[Effects]

The ophthalmic apparatus, the method of controlling the ophthalmic apparatus, and the program according to the embodiments will be explained.

An ophthalmic apparatus (1) according to some embodiments includes an interference optical system (optical system included in the OCT unit 100, optical scanner 42, VCC lens 47), an optical scanner controller (211A), and a correction controller (211B). The interference optical system includes an astigmatism correction optical member (VCC lens 47), and an optical scanner (42). The interference optical system is configured to split light (L0) from a light source (light source unit 101) into measurement light (LS) and reference light (LR), to irradiate the measurement light onto the subject's eye (E) via the astigmatism correction optical member and the optical scanner, and to detect interference light (LC) between returning light of the measurement light from the subject's eye and the reference light. The optical scanner controller is configured to control the optical scanner so as to deflect the measurement light in a horizontal direction and a vertical direction on a plane perpendicular to an optical axis of the interference optical system. The correction controller is configured to control the astigmatism correction optical member so as to correct astigmatism based on a detection result of the interference light obtained by the interference optical system.

According to such a configuration, the information in the horizontal and the information in the vertical direction on the plane perpendicular to the optical axis of the interference optical system can be acquired in a shorter time than the time required for raster scan, and the astigmatism can be corrected. This allows to correct the astigmatism with high precision without being affected by eye movement or other factors, even when the speed of the light source is increased.

In some embodiments, the ophthalmic apparatus further includes an analyzer (231) configured to analyze the detection result of the interference light. The correction controller is configured to control the astigmatism correction optical member based on an analysis result obtained by the analyzer.

According to such a configuration, it becomes possible to correct the astigmatism with high precision in accordance with the detection result of the interference light.

In some embodiments, the ophthalmic apparatus further includes an image forming unit (220) configured to form an image of the subject's eye based on the detection result of the interference light. The analyzer is configured to analyze each of a plurality of divided images obtained by dividing the image in a direction intersecting an A-scan direction. The correction controller is configured to control the astigmatism correction optical member based on a plurality of analysis results for the plurality of divided images.

According to such a configuration, the plurality of divided images is generated by dividing the image of the subject's eye in the direction intersecting the A-scan direction, and the astigmatism correction optical member is controlled based on the plurality of analysis results obtained by analyzing the divided images. Thereby, the astigmatism correction optical member can be controlled based on the more detailed analysis results of the subject's eye. This allows to adjust the astigmatism correction optical member in a short time with high precision and with a simple process.

In some embodiments, the analyzer is configured to calculate an evaluation value corresponding to the analysis result for each of the divided images. The correction controller is configured to control the astigmatism correction optical member based on a statistical value of a plurality of evaluation values for the plurality of divided images.

According to such a configuration, the evaluation value is calculated for each divided image, and the astigmatism correction optical member is controlled based on the statistical value of the plurality of evaluation values for the plurality of divided images. This allows to adjust the astigmatism correction optical member in a short time with high precision and with an even simpler process.

In some embodiments, the ophthalmic apparatus further includes a first display controller (display controller 211C) configured to display the evaluation value or the statistical value calculated by the analyzer on a display means (display apparatus 3, display unit 240A).

According to such a configuration, the divided image with different evaluation value can be easily identified from the plurality of divided images, and can be easily identified the factors of the suitability of the adjustment of the astigmatism correction optical member.

In some embodiments, the optical scanner controller is configured to control the optical scanner so as to scan a second scan range including a first scan range with the measurement light, after controlling the astigmatism correction optical member based on the detection result of the interference light obtained by the interference optical system by controlling the optical scanner so as to scan the first scan range of the subject's eye with the measurement light. The image forming unit is configured to form an image of the subject's eye based on the detection result of the interference light obtained by scanning the second scan range with the measurement light.

According to such a configuration, the astigmatism correction optical member can be controlled in consideration of the detection results of the interference light in the second scan range for forming the image of the subject's eye. This allows to correct the astigmatism for the main imaging (main measurement) with high precision. Further, the scan time required for the first scan range can be shortened by making the first scan range narrower than the second scan range. This allows to correct the astigmatism more precisely.

In some embodiments, the optical scanner controller is configured to correct of a position of the second scan range based on tracking information obtained by tracking the interference optical system for a movement of the subject's eye, and to control the optical scanner so as to scan the corrected second scan range with the measurement light.

According to such a configuration, the astigmatism can be corrected more precisely while tracking the movement of the subject's eye.

In some embodiments, the ophthalmic apparatus further includes a second display controller (display controller 211C) configured to display an image of the subject's eye based on the detection result of the interference light obtained by scanning the second scan range with the measurement light on a display means (display apparatus 3, display unit 240A).

According to such a configuration, the ophthalmic apparatus capable of displaying the image of the subject's eye, in which the astigmatism has been corrected with high precision, on the display means can be provided.

In some embodiments, the interference optical system includes a focusing position changing member (OCT focusing lens 45, OCT focusing driver 45A) arranged on an optical path of the measurement light and configured to be capable of changing a focal position of the measurement light. The correction controller is configured to control the focusing position changing member based on the detection result of the interference light obtained by the interference optical system.

According to such a configuration, the ophthalmic apparatus capable of correcting the astigmatism in a short time with high precision, and adjusting the focusing focal position of the measurement light can be provided.

In some embodiments, the interference optical system includes an optical path length changing member (optical path length changing unit 41, corner cube 114 and reference driver 114A) arranged on an optical path of the measurement light or an optical path of the reference light, and configured to change an optical path length difference between the measurement light and the reference light. The optical scanner controller is configured to control the optical scanner so as to deflect the measurement light in a direction intersecting an optical axis of the interference optical system. The correction controller is configured to control the optical path length changing member based the detection result of the interference light obtained by the interference optical system.

According to such a configuration, the ophthalmic apparatus capable of correcting the astigmatism in a short time with high precision, and adjusting the optical path length difference between the measurement light and the reference light can be provided.

In some embodiments, the interference optical system includes a polarization state changing member (polarization controllers 103 and 118) arranged on an optical path of the measurement light or an optical path of the reference light, and configured to change a polarization state of the measurement light or a polarization state of the reference light. The optical scanner controller is configured to control the optical scanner so as to deflect the measurement light in a direction intersecting an optical axis of the interference optical system. The correction controller is configured to control the polarization state changing member based on the detection result of the interference light obtained by the interference optical system.

According to such a configuration, the ophthalmic apparatus capable of correcting the astigmatism in a short time with high precision, and adjusting the optical path length difference between the measurement light and the reference light can be provided.

In some embodiments, the astigmatism correction optical member is configured to be capable of changing a cylindrical power and a cylindrical axis angle.

According to such a configuration, the astigmatism can be corrected in a short time with high precision by changing the cylindrical power and the cylindrical axis angle.

In some embodiments, the astigmatism correction optical member includes a variable cross cylinder lens.

According to such a configuration, the astigmatism can be corrected in a short time with high precision at low cost, using the variable cross cylinder lens.

In some embodiments, the ophthalmic apparatus further includes a third display controller (display controller) configured to display at least one of the cylindrical power or the cylindrical axis angle on a display means (display apparatus 3, display unit 240A).

According such a configuration, the state of the adjust of the astigmatism can be easily grasped.

In some embodiments, the optical scanner controller is configured to control the optical scanner so as to circularly deflect the measurement light by deflecting the measurement light in the horizontal direction and the vertical direction.

According to such a configuration, the scan speed can be kept almost constant over the entire scan region. This allows to acquire the homogeneous scan results over the entire scan region. As a result, the astigmatism can be corrected with high precision based on the homogeneous scan results. In addition, for example, since it is less affected by the specular reflection from the apex of the objective lens, the astigmatism can be corrected with high precision based on the artifact-free scan results.

In some embodiments, when a diffraction limit is r, a diameter of a circle-shaped scan line on the subject's eye is R, and the number of A-lines in the scan line is N, $(R \times \pi/N) < r$ is satisfied.

According to such a configuration, the number of A-lines can be reduced without decreasing the accuracy of the scan for adjusting the imaging conditions (measurement conditions), and the astigmatism can be corrected with high precision in a shorter time.

A method of controlling an ophthalmic apparatus (1) according to some embodiments is an ophthalmic apparatus including an interference optical system (optical system included in the OCT unit 100, optical scanner 42, VCC lens 47), an optical scanner controller (211A), and a correction controller (211B). The interference optical system includes an astigmatism correction optical member (VCC lens 47) and an optical scanner (42). The interference optical system is configured to split light (L0) from a light source (light source unit 101) into measurement light (LS) and reference light (LR), to irradiate the measurement light onto the subject's eye (E) via the astigmatism correction optical member and the optical scanner, and to detect interference light (LC) between returning light of the measurement light from the subject's eye and the reference light. The method of controlling the ophthalmic apparatus includes a first control step of controlling the optical scanner so as to deflect the measurement light in a horizontal direction and a vertical direction on a plane perpendicular to an optical axis of the interference optical system; and a second control step of controlling the astigmatism correction optical member so as to correct astigmatism based on a detection result of the interference light obtained in the interference optical system by irradiating the measurement light deflected in the first control step onto the subject's eye.

According to such a method, the information in the horizontal and the information in the vertical direction can be acquired in a shorter time than the time required for raster scan or two or more line scans, and the astigmatism can be corrected. This allows to correct the astigmatism with high precision without being affected by eye movement or other factors, even when the speed of the light source is increased.

In some embodiments, the method of controlling the ophthalmic apparatus further includes an analysis step of analyzing the detection result of the interference light. The second control step is performed to control the astigmatism correction optical member based on an analysis result obtained in the analysis step.

According to such a method, it becomes possible to correct the astigmatism with high precision in accordance with the detection result of the interference light.

In some embodiments, the method of controlling the ophthalmic apparatus further includes an image forming step of forming an image of the subject's eye based on a detection result of the interference light. The analysis step is performed to analyze each of a plurality of divided images obtained by dividing the image in a direction intersecting an A-scan direction. The second control step is performed to control the astigmatism correction optical member based on a plurality of analysis results corresponding to the plurality of divided images.

According to such a method, the plurality of divided images is generated by dividing the image of the subject's eye in the direction intersecting the A-scan direction, and the astigmatism correction optical member is controlled based on the plurality of analysis results obtained by analyzing the divided images. Thereby, the astigmatism correction optical member can be controlled based on the more detailed analysis results of the subject's eye. This allows to adjust the astigmatism correction optical member in a short time with high precision and with a simple process.

In some embodiments, the analysis step is performed to calculate an evaluation value corresponding to the analysis result for each of the divided images. The second control step is performed to control the astigmatism correction optical member based on a statistical value of evaluation values for the plurality of divided images.

According to such a method, the evaluation value is calculated for each divided image, and the astigmatism correction optical member is controlled based on the statistical value of the plurality of evaluation values for the plurality of divided images. This allows to adjust the astigmatism correction optical member in a short time with high precision and with an even simpler process.

In some embodiments, the method of controlling the ophthalmic apparatus further includes a first display control step of displaying the evaluation value or the statistical value calculated in the analysis step on a display means (display apparatus 3, display unit 240A).

According to such a method, the divided image with different evaluation value can be easily identified from the plurality of divided images, and can be easily identified the factors of the suitability of the adjustment of the astigmatism correction optical member.

In some embodiments, the method of controlling the ophthalmic apparatus further includes a third control step and a second image forming step. The third control step is performed to control the optical scanner so as to scan a second scan range including a first scan range with the measurement light in the second control step, after controlling the astigmatism correction optical member based on the detection result of the interference light obtained by the interference optical system by scanning the first scan range of the subject's eye with the measurement light in the first control step. The second image forming step is performed to form an image of the subject's eye based on the detection result of the interference light obtained by scanning the second scan range with the measurement light in the third control step.

According to such a method, the astigmatism correction optical member can be controlled in consideration of the detection results of the interference light in the second scan range for forming the image of the subject's eye. This allows to correct the astigmatism for the main imaging (main measurement) with high precision. Further, the scan time required for the first scan range can be shortened by making the first scan range narrower than the second scan range. This allows to correct the astigmatism more precisely.

In some embodiments, the second control step is performed to correct a position of the second scan range based on tracking information obtained by tracking the interference optical system for a movement of the subject's eye, and to control the optical scanner so as to scan the corrected second scan range with the measurement light.

According to such a method, the astigmatism can be corrected more precisely while tracking the movement of the subject's eye.

In some embodiments, the method of controlling the ophthalmic apparatus further includes a second display control step of displaying an image of the subject's eye based on the detection result of the interference light obtained by scanning the second scan range with the measurement light on a display means (display apparatus 3, display unit 240A).

According to such a method, the ophthalmic apparatus capable of displaying the image of the subject's eye, in which the astigmatism has been corrected with high precision, on the display means can be provided.

In some embodiments, the interference optical system includes a focusing position changing member (OCT focusing lens 45, OCT focusing driver 45A) arranged on an optical path of the measurement light and configured to be capable of changing a focal position of the measurement light. The method of controlling the ophthalmic apparatus further includes a fourth control step of controlling the focusing position changing member based on the detection result of the interference light obtained by the interference optical system.

According to such a method, the astigmatism can be corrected in a short time with high precision, and the focal position of the measurement light can be adjusted.

In some embodiments, the interference optical system includes an optical path length changing member (optical path length changing unit 41, corner cube 114 and reference driver 114A) arranged on an optical path of the measurement light or an optical path of the reference light, and configured to change an optical path length difference between the measurement light and the reference light. The method of controlling the ophthalmic apparatus further includes a fifth control step of controlling the optical scanner so as to deflect the measurement light in a direction intersecting an optical axis of the interference optical system; and a sixth control step of controlling the optical path length changing member based on the detection result of the interference light obtained by the interference optical system by irradiating the measurement light deflected in the fifth control step onto the subject's eye.

According to such a method, the astigmatism can be corrected in a short time with high precision, and the optical path length difference between the measurement light and the reference light can be adjusted.

In some embodiments, the interference optical system includes a polarization state changing member (polarization controllers 103 and 118) arranged on an optical path of the measurement light or an optical path of the reference light, and configured to change a polarization state of the measurement light or a polarization state of the reference light. The method of controlling the ophthalmic apparatus further includes a seventh control step of controlling the optical scanner so as to deflect the measurement light in a direction intersecting an optical axis of the interference optical system; and an eighth control step of controlling the polarization state changing member based on the detection result of the interference light obtained by the interference optical system by irradiating the measurement light deflected in the seventh control step onto the subject's eye.

According to such a method, the astigmatism can be corrected in a short time with high precision, and the optical path length difference between the measurement light and the reference light can be adjusted.

In some embodiments, the astigmatism correction optical member is configured to be capable of changing a cylindrical power and a cylindrical axis angle.

According to such a method, the astigmatism can be corrected in a short time with high precision by changing the cylindrical power and the cylindrical axis angle.

In some embodiments, the astigmatism correction optical member includes a variable cross cylinder lens.

According to such a method, the astigmatism can be corrected in a short time with high precision at low cost, using the variable cross cylinder lens.

In some embodiments, the method of controlling the ophthalmic apparatus further includes a third display control step of displaying at least one of the cylindrical power or the cylindrical axis angle on a display means (display apparatus 3, display unit 240A).

According such a method, the state of the adjust of the astigmatism can be easily grasped.

In some embodiments, the first control step is performed to control the optical scanner so as to circularly deflect the measurement light by deflecting the measurement light in the horizontal direction and the vertical direction.

According to such a configuration, the scan speed can be kept almost constant over the entire scan region. This allows to acquire the homogeneous scan results over the entire scan region. As a result, the astigmatism can be corrected with high precision based on the homogeneous scan results. In addition, for example, since it is less affected by the specular reflection from the apex of the objective lens, the astigmatism can be corrected with high precision based on the artifact-free scan results.

In some embodiments, when a diffraction limit is r, a diameter of a circle-shaped scan line on the subject's eye is R, and the number of A-lines in the scan line is N, (R \ n/N)<r is satisfied.

According to such a method, the number of A-lines can be reduced without decreasing the accuracy of the scan for adjusting the imaging conditions (measurement conditions), and the astigmatism can be corrected with high precision in a shorter time.

A program according to some embodiments causes a computer to execute each step of the method of controlling the ophthalmic apparatus of any one of described aboves.

According to such a program, the information in the horizontal and the information in the vertical direction on the plane perpendicular to the optical axis of the interference optical system can be acquired in a shorter time than the time required for raster scan, and the astigmatism can be corrected. This allows to correct the astigmatism with high precision without being affected by eye movement or other factors, even when the speed of the light source is increased.

The configuration described above is only an example for suitably implementing the present invention. Therefore, any modification (omission, substitution, addition, etc.) within the scope of the gist of the present invention can be appropriately applied. The configuration to be employed is selected according to the purpose, for example. In addition, depending on the configuration to be applied, it is possible to obtain the actions and effects obvious to those skilled in the art and the actions and effects described in this specification.

The invention has been described in detail with particular reference to preferred embodiments thereof and examples, but it will be understood that variations and modifications can be effected within the spirit and scope of the invention covered by the claims which may include the phrase "at least one of A, B and C" as an alternative expression that means one or more of A, B and C may be used, contrary to the holding in Superguide v. DIRECTV, 69 USPQ2d 1865 (Fed. Cir. 2004).

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. An ophthalmic apparatus, comprising:
an interference optical system including an astigmatism correction optical member, having an astigmatism correcting lens or mirror, and an optical scanner, and configured to split light from a light source into measurement light and reference light, to irradiate the measurement light onto a subject's eye via the astigmatism correction optical member and the optical scanner, and to detect interference light between returning light of the measurement light from the subject's eye and the reference light;
processing circuitry configured as an optical scanner controller configured to control the optical scanner so as to deflect the measurement light in a horizontal direction and a vertical direction on a plane perpendicular to an optical axis of the interference optical system; and
the processing circuitry further configured as a correction controller configured to control the astigmatism correction optical member so as to correct astigmatism based on a detection result of the interference light obtained by the interference optical system, wherein
the optical scanner controller is configured to control the optical scanner so as to circularly deflect the measurement light by deflecting the measurement light in the horizontal direction and the vertical direction, and
when a diffraction limit is r, a diameter of a circle-shaped scan line on the subject's eye is R, and the number of A-lines in the scan line is N, (R×π/N)<r is satisfied.

2. The ophthalmic apparatus of claim 1, wherein
the processing circuitry is further configured as an analyzer configured to analyze the detection result of the interference light, and
the correction controller is configured to control the astigmatism correction optical member based on an analysis result obtained by the analyzer.

3. The ophthalmic apparatus of claim 2, further comprising an image forming circuitry configured to form an image of the subject's eye based on the detection result of the interference light, wherein the analyzer is configured to analyze each of a plurality of divided images obtained by dividing the image in a direction intersecting an A-scan direction, and the correction controller is configured to control the astigmatism correction optical member based on a plurality of analysis results for the plurality of divided images.

4. The ophthalmic apparatus of claim 3, wherein the analyzer is configured to calculate an evaluation value corresponding to the analysis result for each of the divided images, and the correction controller is configured to control the astigmatism correction optical member based on a statistical value of a plurality of evaluation values for the plurality of divided images.

5. The ophthalmic apparatus of claim 4, wherein the processing circuitry is further configured as a first display controller configured to display the evaluation value or the statistical value calculated by the analyzer on a display.

6. The ophthalmic apparatus of claim 3, wherein the optical scanner controller is configured to control the optical scanner so as to scan a second scan range including a first scan range with the measurement light, after controlling the astigmatism correction optical member based on the detection result of the interference light obtained by the interference optical system by controlling the optical scanner so as to scan the first scan range of the subject's eye with the measurement light, and the image forming circuitry is configured to form an image of the subject's eye based on the detection result of the interference light obtained by scanning the second scan range with the measurement light.

7. The ophthalmic apparatus of claim 6, wherein the optical scanner controller is configured to correct of a position of the second scan range based on tracking information obtained by tracking the interference optical system for a movement of the subject's eye, and to control the optical scanner so as to scan the corrected second scan range with the measurement light.

8. The ophthalmic apparatus of claim 6, wherein the processing circuitry is further configured as a second display controller configured to display an image of the subject's eye based on the detection result of the interference light obtained by scanning the second scan range with the measurement light on a display.

9. The ophthalmic apparatus of claim 1, wherein the interference optical system includes a focusing position changing member having a lens and arranged on an optical path of the measurement light and configured to be capable of changing a focal position of the measurement light, and the correction controller is configured to control the focusing position changing member based on the detection result of the interference light obtained by the interference optical system.

10. The ophthalmic apparatus of claim 1, wherein the interference optical system includes an optical path length changing member having a corner cube and arranged on an optical path of the measurement light or an optical path of the reference light, and configured to change an optical path length difference between the measurement light and the reference light, the optical scanner controller is configured to control the optical scanner so as to deflect the measurement light in a direction intersecting an optical axis of the interference optical system, and the correction controller is configured to control the optical path length changing member based the detection result of the interference light obtained by the interference optical system.

11. The ophthalmic apparatus of claim 1, wherein the interference optical system includes a polarization state changing member arranged on an optical path of the measurement light or an optical path of the reference light, and configured to change a polarization state of the measurement light or a polarization state of the reference light, the optical scanner controller is configured to control the optical scanner so as to deflect the measurement light in a direction intersecting an optical axis of the interference optical system, and the correction controller is configured to control the polarization state changing member based on the detection result of the interference light obtained by the interference optical system.

12. The ophthalmic apparatus of claim 1, wherein the astigmatism correction optical member is configured to be capable of changing a cylindrical power and a cylindrical axis angle.

13. The ophthalmic apparatus of claim 12, wherein the astigmatism correction optical member includes a variable cross cylinder lens.

14. The ophthalmic apparatus of claim 12, further comprising a third display controller configured to display at least one of the cylindrical power or the cylindrical axis angle on a display.

15. A method of controlling an ophthalmic apparatus including an interference optical system including an optical scanner and configured to split light from light source into measurement light and reference light, to irradiate a subject's eye with the measurement light deflected by the optical scanner, and to detect interference light between returning light of the measurement light from the subject's eye and the reference light, the method comprising:

a first control step of controlling the optical scanner so as to deflect the measurement light in a horizontal direction and a vertical direction on a plane perpendicular to an optical axis of the interference optical system; and a second control step of controlling an astigmatism correction optical member so as to correct astigmatism based on a detection result of the interference light obtained in the interference optical system by irradiating the measurement light deflected in the first control step onto the subject's eye, wherein the first control step is performed to control the optical scanner so as to circularly deflect the measurement light by deflecting the measurement light in the horizontal direction and the vertical direction, and when a diffraction limit is r, a diameter of a circle-shaped scan line on the subject's eye is R, and the number of A-lines in the scan line is N, $(R \times \pi/N) < r$ is satisfied.

16. A non-transitory computer readable recording medium storing a program of causing a computer to execute each step of a method of controlling an ophthalmic apparatus including an interference optical system including an optical scanner and configured to split light from light source into measurement light and reference light, to irradiate a subject's eye with the measurement light deflected by the optical scanner, and to detect interference light between returning light of the measurement light from the subject's eye and the reference light, the method comprising:

a first control step of controlling the optical scanner so as to deflect the measurement light in a horizontal direction and a vertical direction on a plane perpendicular to an optical axis of the interference optical system; and a second control step of controlling an astigmatism correction optical member so as to correct astigmatism based on a detection result of the interference light obtained in the interference optical system by irradiating the measurement light deflected in the first control step onto the subject's eye, wherein the first control step is performed to control the optical scanner so as to circularly deflect the measurement light by deflecting the measurement light in the horizontal direction and the vertical direction, and when a diffraction limit is r, a diameter of a circle-shaped scan line on the subject's eye is R, and the number of A-lines in the scan line is N, $(R \times \pi / N) < r$ is satisfied.

* * * * *